(12) United States Patent
Behling et al.

(10) Patent No.: US 11,882,642 B2
(45) Date of Patent: Jan. 23, 2024

(54) PARTICLE BASED X-RAY SOURCE

(71) Applicant: INNOVICUM TECHNOLOGY AB, Stockholm (SE)

(72) Inventors: Rolf Behling, Norderstedt (DE); Mats Danielsson, Täby (SE)

(73) Assignee: Innovicum Technology AB, Stockholm (SE)

( * ) Notice: Subject to any disclaimer, the term of this patent is extended or adjusted under 35 U.S.C. 154(b) by 217 days.

(21) Appl. No.: 17/564,350

(22) Filed: Dec. 29, 2021

(65) Prior Publication Data
US 2023/0209693 A1    Jun. 29, 2023

(51) Int. Cl.
*H05G 2/00*    (2006.01)

(52) U.S. Cl.
CPC .............. *H05G 2/008* (2013.01); *H05G 2/006* (2013.01)

(58) Field of Classification Search
CPC .......... H05G 2/00; H05G 2/008; H05G 2/006; H01J 35/08; H01J 35/24; H01J 2235/082; H01J 2235/086; A61B 6/032; A61B 6/40
See application file for complete search history.

(56) References Cited

U.S. PATENT DOCUMENTS

| | | | |
|---|---|---|---|
| 5,991,360 A | 11/1999 | Matsui et al. | |
| 6,560,313 B1 | 5/2003 | Harding et al. | |
| 7,601,399 B2 | 10/2009 | Bamola et al. | |
| 8,158,960 B2 | 4/2012 | Vaschenko et al. | |
| 8,470,794 B2 | 6/2013 | Jayasena et al. | |
| 9,953,729 B2 | 4/2018 | Watari et al. | |
| 10,192,711 B2 | 1/2019 | Bondarenko et al. | |
| 10,297,359 B2 | 5/2019 | Yun et al. | |
| 10,818,468 B1 | 10/2020 | Hansson et al. | |
| 2010/0294953 A1 | 11/2010 | Vaschenko et al. | |
| 2011/0080997 A1 | 4/2011 | Sukowski et al. | |
| 2013/0301805 A1 | 11/2013 | Hemberg et al. | |
| 2014/0226772 A1 | 8/2014 | Watari et al. | |
| 2017/0221670 A1 | 8/2017 | Bondarenko et al. | |
| 2019/0115184 A1 | 4/2019 | Zalubovsky | |

FOREIGN PATENT DOCUMENTS

| | | |
|---|---|---|
| EP | 1305984 B1 | 11/2010 |
| EP | 2747090 A1 | 6/2014 |
| EP | 3170194 B1 | 5/2019 |
| JP | S61-153936 A | 7/1986 |
| JP | 2001-256909 A | 9/2001 |

(Continued)

OTHER PUBLICATIONS

Eschey et al., "Examination of the powder spreading effect in Electron Beam Melting (EBM)", Proc. of the SFF (Solid Freeform Fabrication) Symposium 99. 308-319 (2009).

(Continued)

*Primary Examiner* — Jurie Yun
(74) *Attorney, Agent, or Firm* — Morgan, Lewis & Bockius LLP

(57) ABSTRACT

An X-ray source (100) comprise a microparticle source (200) configured to generate a particle stream (20) of spatially separated and moving, solid and/or liquid microparticles. The X-ray source (100) also comprises an electron source (300) configured to generate an electron beam (30) of electrons incident onto the particle stream (20) at an interaction region (1) to excite solid and/or liquid microparticles in the interaction region (1) to generate X-rays (10).

37 Claims, 14 Drawing Sheets

(56) References Cited

FOREIGN PATENT DOCUMENTS

| JP | 2004-028845 A | 1/2004 |
|---|---|---|
| JP | 2007-123022 A | 5/2007 |
| RU | 2709183 C1 | 12/2019 |
| WO | 01/31678 A1 | 5/2001 |
| WO | 2006/093687 A1 | 9/2006 |
| WO | 2011/112235 A1 | 9/2011 |

OTHER PUBLICATIONS

Mahale, "Electron Beam Melting of Advanced Materials and Structures" [North Carolina State University, Raleigh, NC, USA]. (2009) https://repository.lib.ncsu.edu/handle/1840.16/4943, 219 pages.
IEC 60336, Electrical and loading characteristics of X-ray tube assemblies for medical diagnosis (5th ed.). International Electrotechnical Commission (Dec. 2020), 44 pages.
Opydo et al., "The role of microparticles in initiating the electric breakdown in high-voltage vacuum insulation systems", Computer Applications in Electrical Engineering, (2016) vol. 14, pp. 177-186, https://doi.org/10.21008/i.1508-4248.2016.0016.
Trottenberg et al., "Feasibility of electrostatic microparticle propulsion", New Journal of Physics, (2008), 10(6), Jun. 30, 2012. https://doi.org/10.1088/1367-2630/10/6/063012.
Wang et al., "A new technique for nanoparticle transport and its application in a novel nano-sieve", Scientific Reports, (2018), 8(1), 9682. https://doi.org/10.1038/s41598-018-28033-5.
International Search Report and Written Opinion dated May 22, 2023, issued in corresponding International Patent Application No. PCT/SE2022/051240.

PARTICLE BASED X-RAY SOURCE

TECHNICAL FIELD

The present invention generally relates to X-ray sources, and in particular to particle-based X-ray sources and X-ray systems comprising such X-ray sources.

BACKGROUND

X-ray sources are comprised in various imaging systems including medical or diagnostic imaging systems and non-medical imaging systems. The former include, for instance, computed tomography (CT) systems that acquire three-dimensional (3D) images of the human body or part thereof noninvasively for diagnostic purposes, e.g., typically employing X-ray attenuation or X-ray phase shift. Correspondingly, non-medical imaging systems are used for various applications including non-destructive testing or gathering chemical or crystallographic information.

There exist various X-ray sources for bremsstrahlung, i.e., braking radiation, which is the most commonly used type of X-rays. Such X-ray sources employ various types of X-ray targets and are used in imaging systems, such as stationary transparent X-ray targets, stationary and rotary reflection targets and X-ray sources based on liquid metal jet anodes. Most prior art X-ray sources have in common that the target, sometimes also called X-ray anode, is conductively connected to a terminal, which supplies a positive electrical potential with respect to the electron source. This electron source, typically called the cathode, generates a beam of electrons that impinges on the target in a defined area, the so-called focal spot. When he discovered X-rays in 1895, Prof. Dr. Conrad Röntgen a fixed glass target, i.e., the glass wall of the tube. The electron current impinging on the glass caused ejection of scattered electrons that balance further charging. Soon after, glass was replaced by metal that allows for a more rugged design, higher X-ray output and a stable electric charge and X-ray spectrum when connected to a high voltage source.

Prior art bremsstrahlung X-ray sources employ the interaction of energized electrons with the nuclei of atoms with kinetic electron energies at impact from about 1 keV to multiple MeV. Medical imaging systems typically operate with energies between 25 keV and 150 keV. The gross efficiency of conversion of electrical power to X-ray intensity is typically in the order of a percent. The efficiency is proportional to the atomic number of the target material and the applied tube voltage. Most of the electron energy is wasted through excitation of plasmons by electron-electron scatter in the target material. The initially produced X-ray intensity from typical thick targets emerges nearly angular isotropic and is proportional to the electron current and about the square of the tube voltage used for producing the electron beam. Due to the energy-dependent attenuation in an object to be imaged, X-ray imaging with minimal radiation dose demands for balancing material contrast and photon flux. Typically, the tube voltage is adjusted for an optimal ratio of contrast-to-noise for a given X-ray dose. The spatial image resolution achievable by the X-ray system depends on the size of the focal spot (FS), i.e., the region where X-rays are created. The FS size depends on the focusing of the electron beam and the geometry of the target that the electrons hit. Enhancing the spatial resolution requires, first, that an enhanced electron current density can be delivered by the cathode. Secondly, the target material must withstand the enhanced local heat loading.

X-ray sources with transparent targets typically employ a conversion layer that is a few μm thick and from a material with high atomic number (Z), for instance tungsten, coated on a heat spreader like beryllium or diamond with low atomic number. This conversion layer is transparent for the generated X-rays, which are detected in the direction of the incoming electrons. Such tubes delivering a wide-angle fan of X-rays are typically used for microfocus magnification imaging techniques or material analysis.

X-ray sources for medical diagnostic imaging usually employ a reflection target comprising a several hundred micrometers thick slab of sintered and forged tungsten. This target is embedded in a stationary copper stem for stationary anode tubes. X-rays are taken out along a central beam that makes a small angle with the plane of the anode at the side where the electrons enter. Although the electrons penetrate the target by only about 2 to 15 μm, the thicker portion of the tungsten slab is necessary to shield the tungsten-copper interface from extreme temperatures at the surface in the FS.

Typical rotating anode X-ray sources comprise a rotatable disk that bears a 0.5 to 1 mm thick conversion layer of 95% tungsten and 5% rhenium, which is covering a body plate from reduced-weight titanium-zirconium-molybdenum (TZM). This body is usually about a centimeter thick and often backed with graphite to enhance the heat storage capacity of the entire target. TZM and similar metal composites allow for angular rotor velocities of up to about 10,000 rpm at body temperatures of up to 1500° C. The safely achievable velocity of the anode track is limited by the burst speed of the anode to about 100 m/s. Such anodes allow for uses in CT applications of 120 kW nominal CT anode input power (for 4 s, every 10 minutes, according to IEC 60613) in an X-ray optical FS of 1.1 mm azimuth and 1.2 mm axial dimension full width at half maximum (FWHM), measured in the central beam at 8° anode angle, which corresponds to physical FS dimensions of 1.1 mm (azimuthal)×9 mm (radial). Liquid metal jet X-ray sources typically employ a gallium-based jet of liquid metal of 200 μm diameter emerging from a nozzle at a velocity of about 70 m/s. This allows for constant power input of up to 1000 W. The physical FS partly wraps around the liquid metal jet with dimensions of typically 120 μm×30 μm. Due to lower atomic number the X-ray conversion efficiency is reduced with respect to tungsten targets by about 50%.

There is ongoing need for X-ray sources capable of producing smaller FS, while maintaining high X-ray intensity to improve the spatial resolution of images or shortening exposure times by enhancing the X-ray output while maintaining high contrast resolution.

SUMMARY

It is a general objective to provide an X-ray source capable of producing small X-ray focal spot dimensions and high X-ray intensity.

This and other objectives are met by embodiments as disclosed herein.

The present invention is defined in the independent claims. Further embodiments of the invention are defined in the dependent claims.

An aspect of the embodiments relates to an X-ray source comprising a microparticle source configured to generate a particle stream of spatially separated and moving, solid and/or liquid microparticles. The X-ray source also comprises an electron source configured to generate a beam of electrons incident onto the particle stream at an interaction region to excite solid and/or liquid microparticles in the interaction region to generate X-rays.

Another aspect of the embodiments relates to an X-ray system comprising an X-ray source according to above.

The X-ray source of the invention is able to produce a high velocity target in the form of a stream of microparticles moving at a high velocity when interacting with a beam of energized electrons to produce used X-rays. The high velocity of the microparticles enables minimizing the dwell time of the microparticles under electron impact. Compared with conventional X-ray sources, the achievable density of electrical input power, the intensity of the generated X-rays and, thus, the brilliance in terms of photon output intensity in relation to the dimensions of the X-ray source volume may be enhanced.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

The present invention generally relates to X-ray sources, and in particular to particle-based X-ray sources and X-ray systems comprising such X-ray sources.

The X-ray source of the invention utilizes fast moving microparticles (μPs) for producing X-rays. Upon impact, energized electrons excite these μPs to generate X-ray brake radiation. Compared with prior art X-ray sources, the achievable high velocity of the μPs enables significantly reduced dwell times of the μPs, i.e., the X-ray target, under electron impact. This allows for superior applicable density of power of interaction, i.e., the power that is converted from the electrical energy of the electron beam, which comprises the tube current, to produced X-rays. Compared with conventional rotating anodes and liquid metal jets, the target velocity, i.e., the μP velocity, can be enhanced by at least an order of magnitude, enabling smaller focal spots or focal volumes at the same high output photon intensity.

Figure 1:
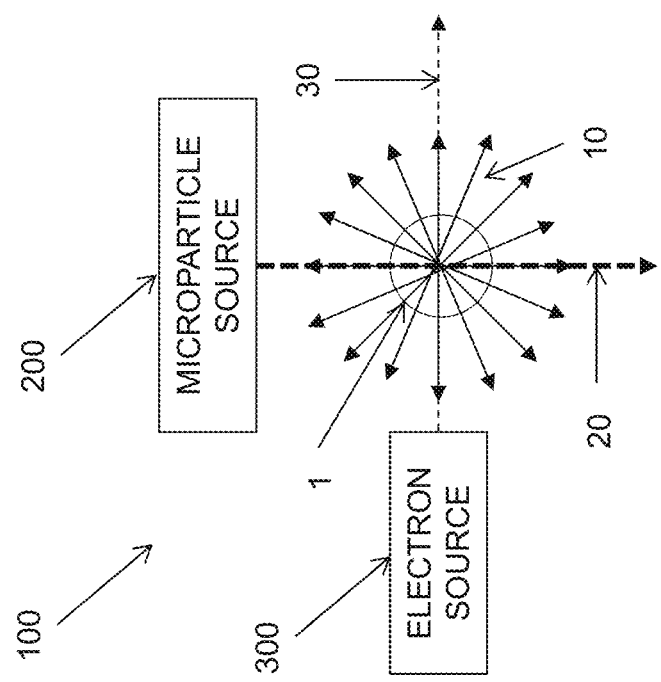
FIG. 1 is a schematic illustration of an X-ray source according to an embodiment.

An aspect of the invention relates an X-ray source 100, see FIG. 1. The X-ray source 100 comprises a microparticle source 200 configured to generate a particle stream 20 of spatially separated and moving, solid and/or liquid microparticles. The X-ray source 100 also comprises an electron source 300 configured to generate an electron beam 30 of electrons incident onto the particle stream 20 at an interaction region 1 to excite solid and/or liquid microparticles in the interaction region 1 to generate X-rays 10.

Typically, X-ray brake radiation is produced in X-ray tubes by the impact of electrons on a target. Instead of solid or liquid targets with permanent electric conductive connection to a high voltage source, the X-ray source 100 of the invention employs a particle stream 20 of electrically floating and fast moving, solid and/or liquid microparticles (μPs). Energized electrons of the electron beam 30 interact with the spatially separated and moving, solid and/or liquid μPs to generate X-rays, typically so-called X-ray brake radiation or bremsstrahlung. The solid and/or liquid μPs are accelerated to high velocities and then exposed to the electron beam 30 at the interaction region 1, which is also referred to herein as the interaction zone 1 herein. The dwell time of the solid and/or liquid μPs under electron impact in the interaction region 1 is preferably minimized. Realistic conditions of μP material, size, kinetic electron impact energy and μP velocity would allow the permitted density of power of interaction at the interaction region 1 to be superior to prior art technologies.

The solid and/or liquid μPs in the particles stream 20 are spatially separated. This means that, at least in the interaction region 1, a majority of the solid and/or liquid μPs are in the form of individual solid µPs and/or individual liquid µPs in the particle stream 20 that are spatially and geometrically (mechanically) separated. Ideally, most of the µPs therefore do not form aggregates or larger liquid droplets but are instead separated from each other as individual solid µPs and/or individual liquid µPs, i.e., droplets.

The µPs in the particle stream 20 could be solid µPs, i.e., µPs in solid form, liquid µPs, i.e., µPs in liquid form, or indeed a combination thereof. Currently preferred µPs are solid µPs. Solid as used herein imply that the µPs are in solid form but do not necessarily have to be uniform or solid in terms of non-porous. Hence, also at least partly porous, solid µPs could be used according to the invention.

The µPs in the particle stream 20 are preferably electrically charged µPs and/or magnetic µPs. In such a case, the charge and/or magnetic properties of the µPs could be utilized to accelerate the µPs to high velocities when reaching the interaction region 1. In an embodiment, the µPs are electrically charged µPs. In another embodiment, the µPs are magnetic µPs. In a further embodiment, the µPs are electrically charged and magnetic µPs. It is currently preferred to use electrically charged µPs, i.e., solid and/or liquid, electrically charged µPs, or electrically charged and magnetic µPs, i.e., solid and/or liquid, electrically charged and magnetic µPs.

Figure 2:
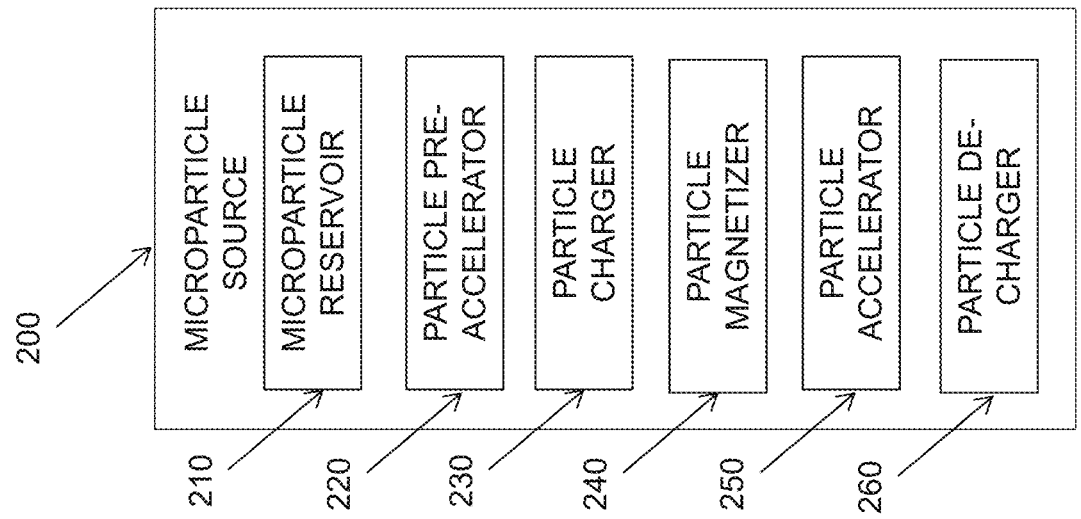
FIG. 2 is a schematic illustration of a microparticle source according to an embodiment.

FIG. 2 is a schematic illustration of a µP source 200 according to an embodiment. In FIG. 2, the µP source 200 is illustrated as comprising different devices or components represented by a µP reservoir 210, a particle pre-accelerator 220, a particle charger 230, a particle magnetizer 240, a particle accelerator 250 and a particle de-charger 260. The µP source 200 may, in various embodiments, comprise one or more of these different devices or components including any combination of two or more of these devices. Hence, embodiments of invention include a µP source 200 comprising the µP reservoir 210, a µP source 200 comprising the particle pre-accelerator 220, a µP source 200 comprising the particle charger 230, a µP source 200 comprising the particle magnetizer 240, a µP source 200 comprising the particle accelerator 250 and a µP source 200 comprising the particle de-charger 260. Further embodiments of the µP source 200 comprises two of these devices or components, such as the µP reservoir 210 and the particle pre-accelerator 220, the µP reservoir 210 and the particle charger 230, the µP reservoir 210 and the particle magnetizer 240, the µP reservoir 210 and the particle accelerator 250, the µP reservoir 210 and the particle de-charger 260, the particle pre-accelerator 220 and the particle charger 230, the particle pre-accelerator 220 and the particle magnetizer 240, the particle pre-accelerator 220 and the particle accelerator 250, the particle pre-accelerator 220 and the particle de-charger 260, the particle charger 230 and the particle magnetizer 240, the particle charger 230 and the particle accelerator 250, the particle charger 230 and the particle de-charger 260, the particle magnetizer 240 and the particle accelerator 250, the particle magnetizer 240 and the particle de-charger 260, and the particle accelerator 250 and the particle de-charger 260. In additional embodiments, the µP source 200 comprises three of these devices or components, such as the µP reservoir 210, the particle pre-accelerator 220 and the particle charger 230; the µP reservoir 210, the particle pre-accelerator 220 and the particle magnetizer 240; the µP reservoir 210, the particle pre-accelerator 220 and the particle accelerator 250; the µP reservoir 210, the particle pre-accelerator 220 and the particle de-charger 260; the µP reservoir 210, the particle charger 230 and the particle magnetizer 240; the µP reservoir 210, the particle charger 230 and the particle accelerator 250; the µP reservoir 210, the particle charger 230 and the particle de-charger 260; the µP reservoir 210, the particle magnetizer 240 and the particle accelerator 250; the µP reservoir 210, the particle magnetizer 240 and the particle de-charger 260; the µP reservoir 210, the particle accelerator 250 and the particle de-charger 260; the particle pre-accelerator 220, the particle charger 230 and the particle magnetizer 240; the particle pre-accelerator 220, the particle charger 230 and the particle accelerator 250; the particle pre-accelerator 220, the particle charger 230 and the particle de-charger 260; the particle charger 230, the particle magnetizer 240 and the particle accelerator 250; the particle charger 230, the particle magnetizer 240 and the particle de-charger 260; the particle charger 230, the particle magnetizer 240 and the particle de-charger 260. It is also possible to have a µP source 200 comprising four of these devices or components, such as the µP reservoir 210, the particle pre-accelerator 220, the particle charger 230 and the particle magnetizer 240; the µP reservoir 210, the particle pre-accelerator 220, the particle charger 230 and the particle accelerator 250; the µP reservoir 210, the particle pre-accelerator 220, the particle charger 230 and the particle de-charger 260; the µP reservoir 210, the particle charger 230, the particle magnetizer 240 and the particle accelerator 250; the µP reservoir 210, the particle charger 230, the particle magnetizer 240 and the particle de-charger 260; the µP reservoir 210, the particle pre-accelerator 220, the particle magnetizer 240 and the particle accelerator 250; the µP reservoir 210, the particle pre-accelerator 220, the particle magnetizer 240 and the particle de-charger 260; the particle pre-accelerator 220, the particle charger 230, the particle magnetizer 240 and the particle accelerator 250; the particle pre-accelerator 220, the particle charger 230, the particle magnetizer 240 and the particle de-charger 260; the particle charger 230, the particle magnetizer 240, the particle accelerator 250 and the particle de-charger 260. It is also possible to have a µP source 200 comprising five of these devices or components, such as the µP reservoir 210, the particle pre-accelerator 220, the particle charger 230, the particle magnetizer 240 and the particle accelerator 250; the µP reservoir 210, the particle pre-accelerator 220, the particle charger 230, the particle magnetizer 240 and the particle de-charger 260; the particle pre-accelerator 220, the particle charger 230, the particle magnetizer 240, the particle accelerator 250 and the particle de-charger 260; µP reservoir 210, the particle charger 230, the particle magnetizer 240, the particle accelerator 250 and the particle de-charger 260; µP reservoir 210, the particle pre-accelerator 220, the particle magnetizer 240, the particle accelerator 250 and the particle de-charger 260; µP reservoir 210, the particle pre-accelerator 220, the particle charger 230, the particle accelerator 250 and the particle de-charger 260, or indeed all six of the devices or components, i.e., the µP reservoir 210, the particle pre-accelerator 220, the particle charger 230, the particle magnetizer 240, the particle accelerator 250 and the particle de-charger 260.

In a currently preferred embodiment, the µP source 200 comprises at least the µP reservoir 210 and the particle accelerator 250. In another preferred embodiment, the µP source 200 comprises at least the µP reservoir 210, the particle charger 230 and the particle accelerator 250. In yet another preferred embodiment, the µP source 200 comprises at least the µP reservoir 210, the particle pre-accelerator 220, the particle charger 240 and the particle accelerator 250.

The X-ray source 100 comprises a µP source 200 configured to generate a particle stream 20 of spatially separated and moving, solid and/or liquid µPs. In an embodiment, the µPs detach from the µP reservoir 210 and lose electrical contact when they are electrically charged by the particle charger 230 or before they are individually magnetized by the particle magnetizer 240. In an embodiment, the μP pre-accelerator 220 accelerates the μPs from very low or zero velocity to a base or intermediate velocity. In this state, the μPs may still be in touch with each other such that the particle stream 20 may be pumped and/or pressurized. The μP charger 230 may then induce electric charge to the μPs. Such an electric charge may be induced onto neutral μPs and also onto magnetizable μPs, which then are electrically charged in addition to having an induced magnetic moment. μPs comprising dielectric material may also be polarized and accelerated in a gradient electric field. In an embodiment, the μPs are made of or comprise a magnetizable material and may then be magnetized by the particle magnetizer 240.

Figure 12:
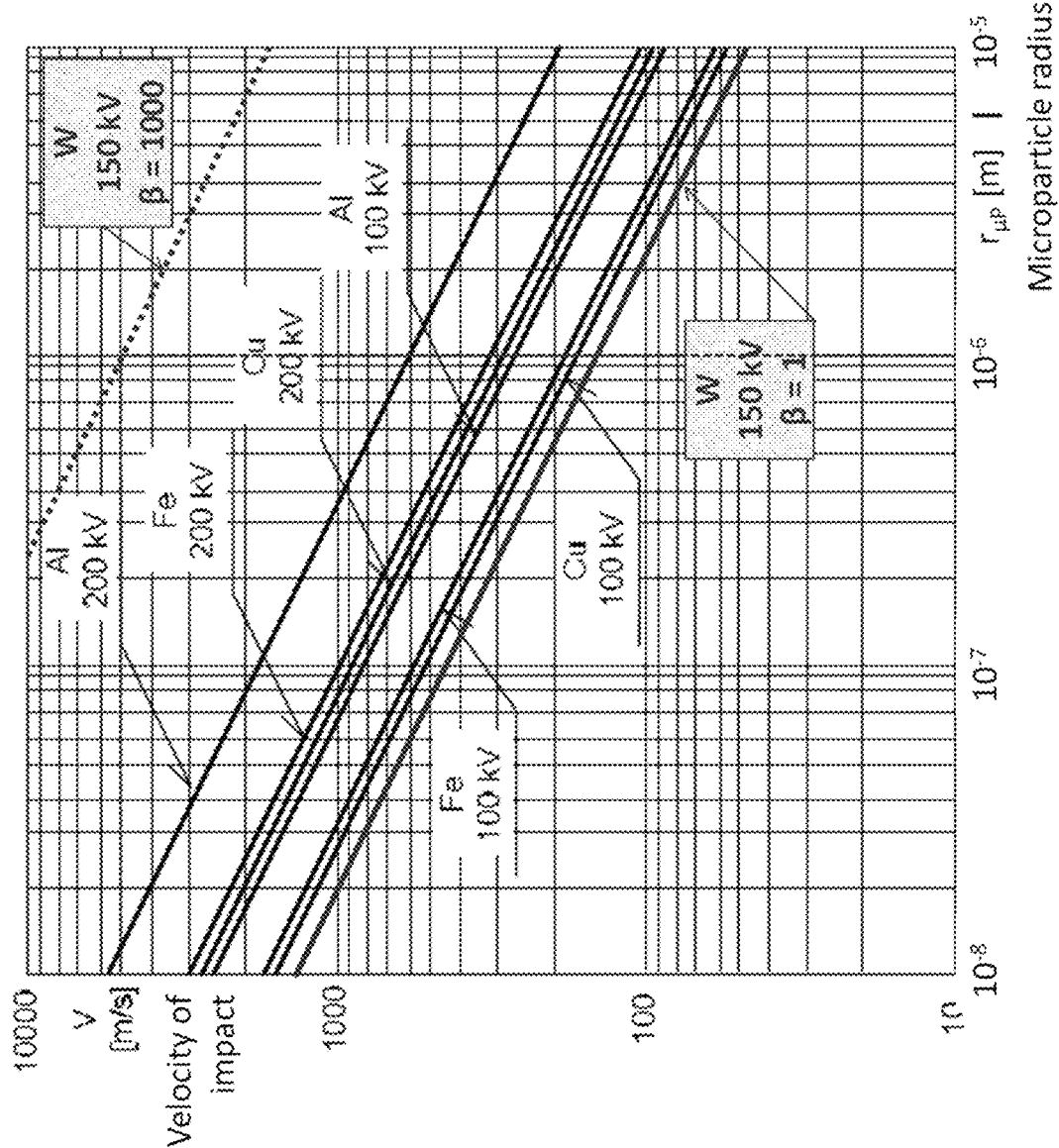
FIG. 12 is a diagram illustrating velocities v vs. radii $r_{\mu P}$ of spherical microparticles of copper, aluminum, iron, and tungsten after acceleration in a 5 mm wide gap charged with the indicated high voltage. The achievable velocity for tungsten microparticles of radius 10 μm and β=1000 would be 1600 m/s. Figure adapted from (Opydo & Opydo, 2016).

The μPs become separated, which is preferred to achieve an intense acceleration by the particle accelerator 250. After leaving the particle accelerator 250, the μPs have gained sufficient kinetic energy to pass the interaction region 1 without destruction by vaporization. After having passed the particle accelerator 250, the μPs may optionally enter the particle de-charger 260. The particle de-charger 260 is then arranged to reduce excessive electric charge from the μPs. It may also serve to, at least partially, de-magnetize magnetized μPs. Accordingly, the particle de-charger 260 could operate to reduce electric charge of the μPs, reduce magnetic moment of the μPs, or both. After acceleration to a desired velocity by the particle accelerator 250 and the particle pre-accelerator 220, further acceleration may not be necessary. Hence, the electrical charge and/or magnetic moment of the μPs could be reduced as it is no longer needed in order to accelerate the μPs further. Such a reduction of electrical charge and/or magnetic moment may in fact be beneficial prior to entering the interaction region 1. Highly charged μPs of the same polarity repel each other. Thus, reduction of electrical charge may prevent the particle stream 20 from expansion before entering the interaction region 1. Correspondingly, magnetized μPs may experience aggregation by magnetic attraction. De-magnetizing may keep the μPs substantially separate in the particle stream 20 when entering the interaction region 1. Keeping the μPs separated and preventing aggregation is beneficial for balancing the μP charge state during interaction with electrons in the interaction region 1. Under controlled conditions, the electrically charged μPs keep their polarity in the interaction region 1 by electron backscattering and ejection of excited initially μP-interior electrons. These processes depend on the size of the μPs and the kinetic energy of the impinging electrons, as depicted in FIG. 12. Space charge of the entire particle stream 20 may also be reduced by the de-charger 260, such that the electric potential of the particle stream 20 and its tendency for expansion are reduced. The de-charger 260 may alternatively, or in addition, be arranged upstream of the interaction region 1 but then preferably downstream of the particle accelerator 250.

After acceleration the particle stream 20 enters the interaction region 1. The interaction region 1, i.e., the origin of the useful X-rays 10, is the at least one intersection of the two streams: the electron beam 30, characterized by the tube current, and the particle stream 30 comprising fast moving μPs.

Figure 15:
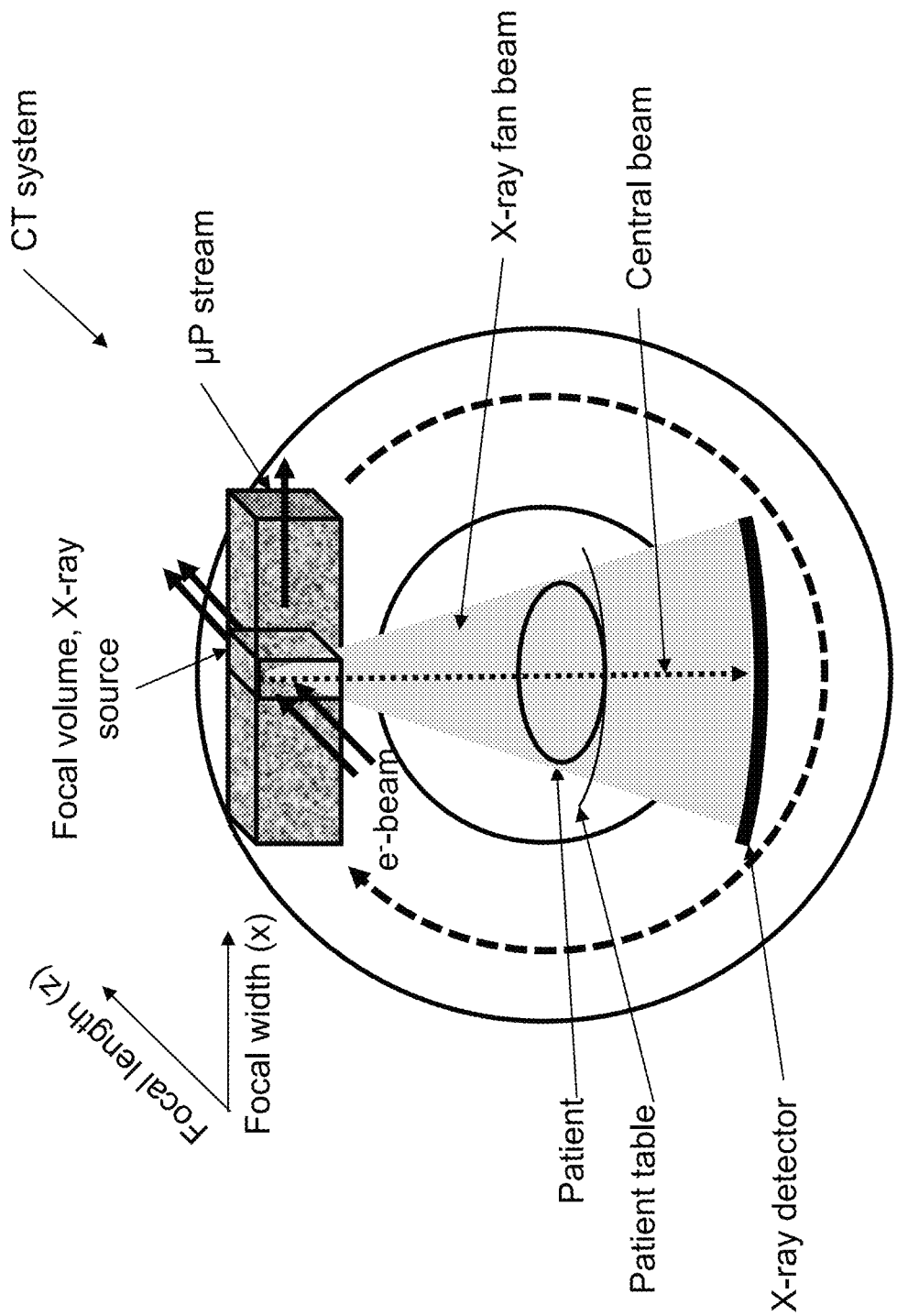
FIG. 15 depicts the focal volume where X-rays are generated in a CT system, i.e., the interaction region where an exemplary μP stream and an electron beam intersect.

The focal spot (FS) size of an X-ray source for medical diagnostic application is defined by the standard IEC 60336, see (IEC60336, 2020). It defines the length of the FS as the projected dimension of the X-ray optical FS that is measured in the long direction of the X-ray source housing assembly. The X-ray optical FS projection of the physical FS is taken onto a plane normal to the central beam and, typically, parallel with the X-ray detector plane. This long direction is in most cases oriented parallel to the electron beam and for rotating anode tubes coincides with the direction of the angular moment of the anode rotor. This long direction is typically denoted as z-axis or axial direction, see FIG. 15 for an exemplary CT system. The corresponding FS dimension is called the FS length. The FS width is measured along the orthogonal direction, typically denoted as azimuthal or x-axis. The definitions of the IEC 60336 standard will be applied herein. Due to the reduced material density of the μP target and as the volume of the intersection of the electron beam 30 and the particle stream 20 has a considerable thickness, the source region is, however, better described by a focal volume instead of a two-dimensional planar FS. The entire particle stream 20 in the electron-flooded volume is radiating X-rays 10. The planar cross section of the electron beam with a conventional target impact area, that for conventional X-ray sources fully characterizes the focal dimension, must, additionally, be accompanied by specifying the thickness of the particle stream 20. For an optimal match in terms of economy of power, it is advised to match the width of the particle stream 20 with the length of the desired focal volume irradiated by the electron beam 30. It is preferred to reduce the thickness of the particle stream 20 in the interaction region 1 to a value at or below the length of the projected desired focal spot. Reducing the thickness of the focal volume by reducing the thickness of the particle stream 20 and, hence, the principal conversion layer, see below, for the sake of enhancing the spatial resolution usually reduces the primary electrical conversion efficiency of the μP based X-ray source 100 for a single pass of the electrons. It is advised to balance this by enhancing the electron current density and optimizing the electronic energy recuperation.

The interaction region 1 is preferably fed with a sufficiently high flux of μPs. Conventionally, X-rays for medical imaging are created in the top 2 to 3 μm of a solid tungsten target where electrons still have nearly maximal energy, see (Behling, 2021), i.e., the so-called principal conversion layer. Deeper layers, e.g., down to a depth of 10 to 15 μm for tube voltages of up to 150 kV, experience traffic of less energetic electrons, which only contribute to the X-ray output with photons of reduced energy. In typical medical application, most of such photons are cancelled from the used X-ray beam by intrinsic absorption in the dense target material or by additional filtration, e.g., using few mm thick slabs of aluminum. For the X-ray source 100 of the invention, the total (summed-up in the direction of the electron beam 30) μP material in the particle stream 20 at the interaction region 1 that is flooded with electrons is preferably at least as thick in total as the principal conversion layer in a conventional source, i.e., 2 to 3 μm for 150 kV maximal tube voltage. Otherwise, the electron beam density would have to be enhanced to balance such a deficit and to obtain high X-ray output.

If the electron beam 30 passes the particle stream 20 other than orthogonally, say under an angle larger than zero but smaller than 90°, the thickness would be measured along a line that makes that an angle with the particle stream 20. Translated to the situation with a particle stream target, this means that if the μPs passing the interaction region 1 were instantly collected, and those located along a line parallel to the electron beam 30 would be attracted by and compacted, say on a plane that is substantially orthogonal to electron beam 30, the thickness of the layer of collected μPs stacked upon each other should correspond to the desired thickness of a defined principal conversion layer. In other words, the integrated travel length of electrons through the µP material in the particle stream 20 (vacuum space excluded) should be of the same length as the dimension of the principal conversion layer. Electrons scattered in the particle stream 20 may get lost from the interaction region 1. These electrons that escape into vacuum will not contribute to X-ray generation. The ratio of lost electrons will depend on the specific geometry of the particle stream 20. It is preferred to specify the parameters of the particle stream 20, e.g., µP size, µP flux, µP velocity, width and thickness of the particle stream 20, such that the scatter loss of electrons is, at least partially, balanced by thickening the particle stream 20 and enhance the calculated principal conversion layer of this µP target with respect to a conventional dense target. Principal conversion layers may e.g., be 5 µm thick for tube voltages of 250 kV. In the limit of a very thin particle stream 20 the principal conversion layer of a µP target may be set equal to a conventional one.

It is, moreover, preferred to adapt the thickness of the interaction region 1, i.e., the thickness of the particle stream 20, to the tube voltage. Due to increasing transparency of µPs for electrons, higher tube voltages will generally demand for thicker principal conversion layers.

The discrete nature of a µP target of the invention may cause fluctuations of the output signal. It is therefore preferred to enhance the number of µPs, i.e., the flux in numbers of µPs per unit cross section of the particle stream 20 and unit time, to reduce the noise arising from the discrete nature. Given a desired thickness of the principal conversion layer, it may be preferred to use µPs of small size in the particle stream 20 and enhance their flux in terms of the number of moving µPs.

There may be instances when it is preferred to keep the width of the particle stream 20 smaller than the corresponding dimension of the electron beam 30. This may be beneficial when focusing the electron beam 30 is difficult.

There may be other instances when it is preferred to use a particle stream 20 of larger width than the electron beam 30. This would be beneficial to realize focal spot wobbling, i.e., the temporal change of the position of the focal area or focal volume. Such technique is widely used for CT applications to reduce aliasing caused by the limited spatial resolution of the CT detector. The electron beam 30 is deflected magnetically and/or electrically to hit different positions on the target. Multiple X-ray projections may be taken instead of a single one. Such a concept can also be applied with the X-ray source 100 of this invention. While wobbling in azimuthal direction, i.e., along the length of the particle stream 20, is possible with a particle stream 20 where length of the electron beam 30 matches the width of the particle stream 20, axial (z) wobbling is possible when the particle stream 20 is wider than the length of a single FS.

Provided that the number of µPs in particle stream 20 and the cross-sectional dimension of the particle stream 20 are constant, the spatial density of µPs, i.e., the number of µPs that exist in a volume, decreases inversely proportional with their velocity. High velocity is a key to minimize µP dwell time in the interaction region 1 and the rise of µP temperature. On the other hand, it is preferred to obtain sufficient interaction with electrons to generate X-rays 10 and, thus, to obtain a minimal density in the interaction region 1, i.e., a sufficiently large principal conversion layer. In addition, the velocity of the µPs should be maximal or close to maximal in the interaction region 1.

To cope with the reduction of the density during acceleration, it is preferred to begin accelerating the µPs from near stand-still from the µP reservoir 210 by engaging µP material at highest possible density. A mechanical pump may serve this objective. This means that the µPs will touch each other or constitute a flow of liquid before dissolving into µP droplets or into segregated solid µPs. Such high density of the material enables mechanical pre-acceleration and pressurizing the material. Gravitational or centrifugal forces may support the pumping action. Centrifugal acceleration in a modern CT system may exceed 30 g, where g denotes the acceleration of gravity. The X-ray source 100 may be constructed such that µPs experience this acceleration as part of pre-acceleration. Free fall in vacuum under the action of centrifugal acceleration of 30 g alone would yield a µP velocity of about 10 m/s, which is comparable to the focal track velocity of a low power rotating anode X-ray tube.

The different devices or components of the µP source 200 shown in FIG. 2 will now be described in more detail below.

In an embodiment, the µP source 200 comprises a particle accelerator 250 configured to accelerate the solid and/or liquid µPs to an average velocity of solid and/or liquid µPs in the interaction region 1 equal to or exceeding a minimum average velocity.

This minimum average velocity is preferably defined to minimize the dwell time of the µPs in the interaction region 1, which in turn leads to a high permitted density of power of interaction, i.e., the power converted into, among others, X-radiation during interaction with the electron beam 30. In a preferred embodiment, the dwell time of the µPs in the interaction region 1 is no more than 10 µs, preferably no more than 7.5 µs and more preferably no more than 5 µs. It is generally preferred to have even lower dwell times of the µPs in the interaction region 1, such as no more than 2.5 µs and preferably no more than 1 µs. Given dimensions of the interaction region 1 of, typically, about a few mm or less in each direction, such as suitable for medical imaging, such low dwell times can be achieved by µPs having an average velocity in the interaction region 1 of at least 100 m/s, preferably at least 250 m/s, and more preferably at least 500 m/s. In a preferred embodiment, the µPs have an average velocity in the interaction region of at least 750 m/s, and more preferably at least 1000 m/s. Hence, in a particular embodiment, the minimum average velocity as referred to above is preferably 100 m/s, preferably 250 m/s, and more preferably 500 m/s, such as 750 m/s, and even more preferably 1000 m/s.

The µPs could be accelerated by the particle accelerator 250 by means of mechanical force, electric force, magnetic force or any combination thereof. As is further described herein, the µPs are preferably pre-accelerated, preferably mechanically pre-accelerated, by the particle pre-accelerator 220 before being accelerated, preferably electrically and/or magnetically accelerated, by the particle accelerator 250.

In an embodiment, the particle accelerator 250 comprises a mechanical particle accelerator configured to apply a mechanical force onto the solid and/or liquid µPs to accelerate the solid and/or liquid µPs.

In a preferred embodiment, the mechanical particle accelerator comprises at least one rotating member having at least one envelope surface configured to engage incident µPs and transfer kinetic energy to the µPs.

µPs incident upon the envelope surface(s) of the rotating member are thereby accelerated by the transfer of kinetic energy from the rotating member into the µPs. The at least one rotating member may, in an embodiment, be in the form of at least one cylinder having a respective envelope or outer surface. The envelope surface of the at least one cylinder may optionally comprise surface structures configured to engage the incident µPs. Such surface structures generally improve the transfer of kinetic energy from the rotating member into the µPs and thereby lead to a more efficient acceleration of the µPs as compared to using cylinders with smooth envelope surfaces. Another example of a rotating member that could be used to accelerate the µPs is at least one rotating member or rotor comprising at least one groove in an envelope surface of the at least one rotating member. In such a case, the rotating member(s) may comprise a single groove around the diameter of the rotating member or multiple parallel grooves. It is also possible to use a spiral groove extending around the diameter of the rotating member as a spiral from one point on the envelope surface to another point on the envelope surface along a rotation axis of the rotating member. The rotating member with groove has the advantage of keeping the µPs in the groove(s) during acceleration and thereby pushing the µPs in a radial and tangential direction when the µPs are directed towards an inner radius inside the at least one groove. The µPs are kept in the at least one groove during a period until they reach the outer radius of the rotating member, thereby experiencing mutual hits and wall contacts and absorbing kinetic energy from the rotating member. Additionally, the at least one groove prevents or at least significantly restricts the µPs from escaping the at least one rotating member in an uncontrolled manner.

It is also possible to use a multiple rotating members arranged in vicinity of each other and rotating with opposite momenta of inertia.

In an embodiment, the rotating member may comprise a mechanical expeller to accelerate the µPs when leaving the rotating member.

Another example of a mechanical particle accelerator that could be used is a mechanical particle accelerator comprising at least one translational mechanical conveyor configured to engage incident µPs and transfer kinetic energy to the µPs.

A further example of a mechanical particle accelerator that could be used is a mechanical particle accelerator comprising at least one pump for liquids, for instance a membrane pump, a piston pump or a centrifugal pump, and a nozzle, configured to engage liquid and transfer kinetic energy to the at least partially liquid µPs.

In an embodiment, the mechanical particle accelerator may comprise at least one membrane, e.g., comprised of graphene. µPs may be accelerated by means of a sliding block that modulates Van-der-Walls forces acting on the membrane, see (Wang et al., 2018). Such interaction may result in accelerating µPs, transporting µPs to desired positions, and narrowing the distributions of µP velocities and µP sizes.

In an embodiment, the µPs are magnetic, i.e., solid and/or liquid, magnetic µPs. The expression solid and/or liquid, magnetic µPs as used herein also encompass solid and/or liquid, electrically charged and magnetic µPs. For instance, the µPs could comprise a ferromagnetic material, a paramagnetic material and/or a diamagnetic material. In such a case, the particle accelerator 240 comprises a magnetic particle accelerator configured to generate a gradient magnetic field to accelerate the solid and/or liquid, magnetic µPs. The µPs may be permanent magnetic µPs or magnetizable µPs to become magnetized or magnetic µPs.

Figure 6:
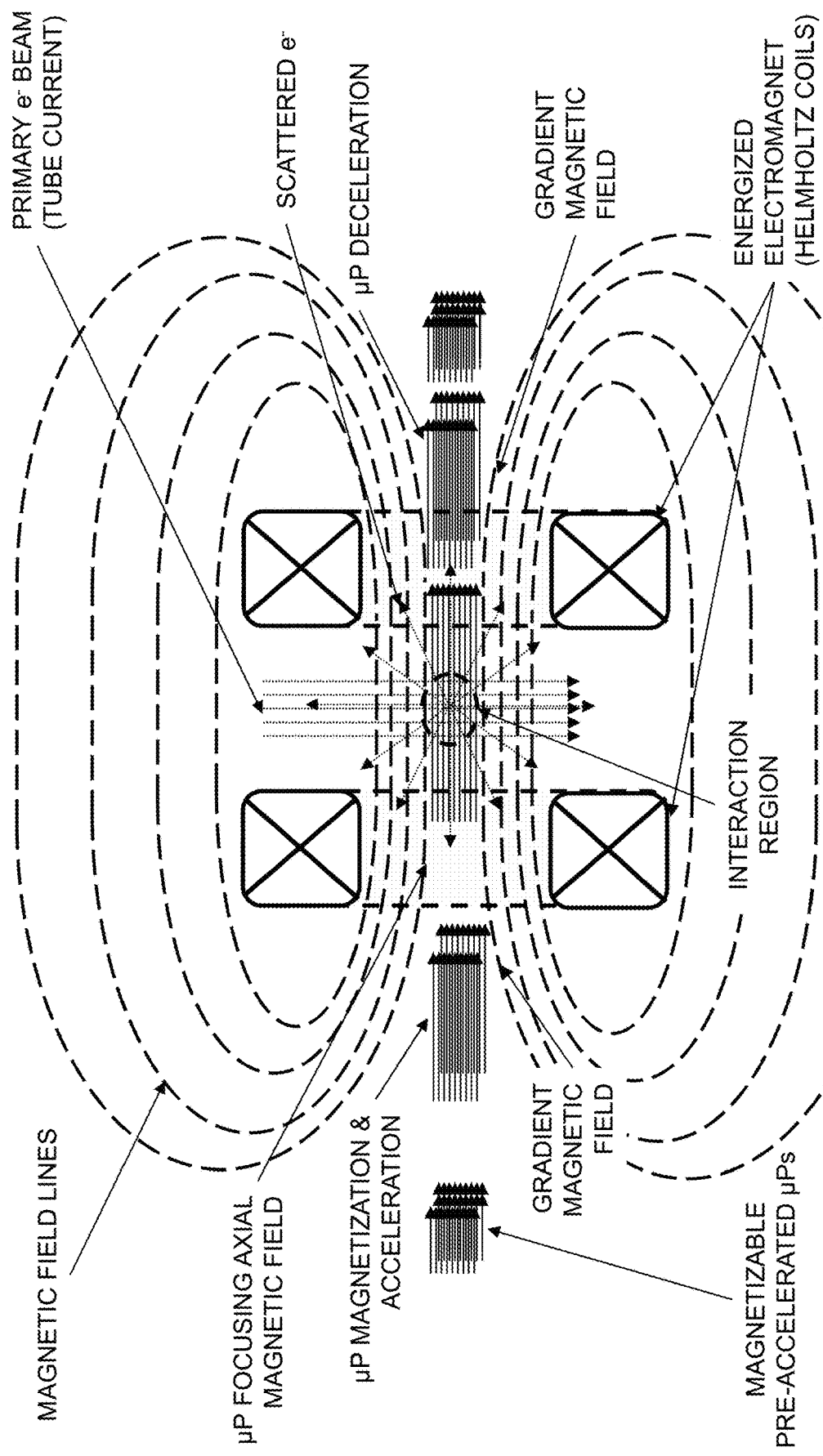
FIG. 6 is a schematic illustration of μP magnetization, acceleration, focusing and deceleration in an X-ray source according to an embodiment.

FIG. 6 schematically shows an arrangement for magnetization, acceleration and decelerating magnetizable µPs. The gradient magnetic field generated by the magnetic particle accelerator thereby accelerates the solid and/or liquid, magnetic µPs when exposed to the gradient magnetic field. The magnetic particle accelerator may then generate the gradient magnetic field in a magnetic coil system, such as a Helmholtz coil. It is also, or alternatively, possible to have a magnetic particle accelerator configured to generate a moving magnetic field in multiple electromagnets, such as a rotating magnetic field. Another example is a spatially progressing magnetic field generated by a set of independently energized electromagnets arranged in series. Such a rotating and/or spatially progressing magnetic field will not only accelerate the µPs but may also cause the µPs to rotate or accelerate bunches of µPs. Rotation of the µPs enables a higher heat take-up and dissipation from the µPs.

Furthermore, an axial magnetic field may be arranged to focus magnetic µPs. Such an axial magnetic field exists, e.g., in the center of a Helmholtz coil system, but may also be arranged in a separate element of the X-ray source 100. It may be beneficial that the µPs enter the magnetic particle accelerator pre-accelerated, as indicated in FIG. 6. The µPs will then leave the magnetic particle accelerator with an average velocity equal to or exceeding the minimum velocity. As the µPs pass the interaction region 1, where they are typically heating up upon interaction with the electron beam 30, and as the magnetic moment of ferromagnetic material typically decreases or even vanishes with rising temperature, the output velocity of the µPs from the deceleration region will typically be higher than the velocity of the µP at the entrance of the interaction region 1.

In an embodiment, the magnetic particle accelerator may employ a gradient magnetic field, such that the magnetic µPs experience a focusing force.

In an embodiment, the magnetic particle accelerator may employ a magnetic field substantially oriented axial with the particle stream 20, such that the magnetic µPs experience a focusing force.

In a preferred embodiment, the particle accelerator 250 comprises an electric particle accelerator configured to generate an electric field to accelerate solid and/or liquid, electrically charged µPs. Hence, in this embodiment, the µPs are electrically charged µPs, i.e., solid and/or liquid, electrically charged µPs. The expression solid and/or liquid, electrically charged µPs, as used herein, also encompass solid and/or liquid, electrically charged and magnetic µPs.

The electric particle accelerator could, for instance, generate a substantially constant electrostatic field, a pulsed electric field or a dynamic high frequency electromagnetic field superimposed with an electrostatic field to accelerate the µPs.

In an embodiment, the electric particle accelerator comprises at least two electrodes at different potentials to generate a respective electric field between two adjacent electrodes of the at least two electrodes. Hence, the electric particle accelerator could be arranged to provide a single-step acceleration or a multistep acceleration. In the former case, the electric particle accelerator comprises a pair of electrodes at different potentials to generate an electric field between the electrodes and where this electric field is configured to accelerate the solid and/or liquid, electrically charged µPs, see FIGS. 3 and 4. Alternatively, the µPs may be accelerated in multiple steps in a series of electrodes at different potentials. In such an embodiment, the electric particle accelerator comprises a plurality of electrodes, such as arranged in a stack of electrodes. This has the additional advantage of applying different electric fields between adjacent electrodes. The field strength can be adjusted to optimize the electrical stability of the multiple accelerating gaps between the electrodes and minimize the risk of vacuum discharges. Moreover, the field strength may vary over time in different phases in the different accelerating gaps such that bunches of µPs may be accelerated. This process would be like the acceleration of ions or electrons in a multi-cavity linear accelerator. The peak field strength "travels" along the direction of the bunches of µPs and time-wise synchronized with those. A multi-electrode concept for acceleration of µPs, be it a stream or bunches, solves a potential problem with pollution of uncontrolled µPs attaching on electrode surfaces. Such µP pollution on electrode surfaces is expected to be higher in the upstream region, i.e., at the region where the acceleration starts as compared to the downstream regions, i.e., at the end of the acceleration region and closer to the interaction region 1. In such an approach, electrode pairs of the electric accelerator or stack of electrodes experiencing the least µP pollution may carry higher electric fields as compared to the upstream electrode pair(s) experiencing more µP pollution. This reduces the risk of vacuum discharges but still provides efficient electric acceleration of the µPs to high velocities.

The electric particle accelerator may employ curved electrodes to generate a focusing electric force on the µPs in the particle stream 20. The focusing force may serve to at least partially compensate for the repelling force that electrically charged µPs of equal polarity excerpt on each other and it may, therefore, reduce the cross section of the particle stream 20.

As mentioned in the foregoing, the µPs could be accelerated by a combination of mechanical force, magnetic force and/or electric force. In such embodiment, the particle accelerator 250 could comprise the above-described mechanical particle accelerator and magnetic particle accelerator, the above-described mechanical particle accelerator and electric particle accelerator, the above-described magnetic particle accelerator and electric particle accelerator, or indeed the mechanical particle accelerator, magnetic particle accelerator and electric particle accelerator. In a currently preferred embodiment, the particle accelerator 250 comprises the electric particle accelerator or a combination of the magnetic particle accelerator and the electric particle accelerator.

For electrically charged µPs, the velocity v of a µP of mass m, detached from a plane surface, accelerated in the gap between electrodes charged with the voltage U is upon reaching the counter-electrode (Latham, 1995):

$$v = \left(\frac{2QU}{m}\right)^{\frac{1}{2}} \quad (1)$$

For $$m = \frac{4}{3}\pi r_{\mu P}^3 \delta_{\mu P},$$

where $\delta_{\mu P}$ is the density of the material of the µP, β the field enhancement factor during charging at detachment from an asperity of the source electrode or by ionization in flight, the velocity while passing the counter electrode positioned at a distance d will be $$v = \pi U \left(\frac{\beta \varepsilon_0}{r_{\mu P} \delta_{\mu P} d}\right)^{\frac{1}{2}} \quad (2)$$

FIG. 12 depicts the relationship between particle size, material density, tube voltage and final velocity after acceleration. According to FIG. 12, a voltage of 150 kV across a gap of 5 mm between plane electrodes would result in a velocity of about 650 m/s upon arrival at the opposite electrode, see (Opydo & Opydo, 2016). The typical gap width required for reliable insulation of 150 kV in commercial X-ray tubes is about 20 mm. This larger gap reduces the electric field strength, the charge Q, and the final velocity to about 300 m/s.

To further enhance the velocity, it is advised to strengthen the electric field at the charging position, reduce the µP size, raise the accelerating voltage and/or use other means to raise the final velocity. The electric field may be further intensified by local field enhancing structures, e.g., protrusions, and detaching the µPs from their apexes. The µP charge may also be enhanced by active charging, e.g., through ion bombardment for positive charging. Bombardment with auxiliary electrons of sufficiently low energy may be used for negative charging, whereby the kinetic electron energy at impact would result in a backscattering yield below unity. Alternatively or in addition, a dielectric expeller may be used, as described below.

In an embodiment, the particle source 200 comprises a µP reservoir 210. The µP reservoir 210 is then configured to comprise solid µPs or a liquid. In the latter case, the liquid µPs are formed or produced from this liquid. As is further described herein, the liquid may comprise solid µPs. The µP reservoir 210 could be in the form of any container configured to contain and store the solid µPs or the liquid. The µP reservoir 210 preferably has a closable inlet/outlet or opening that can be opened and closed. In such a case, the inlet/outlet is preferably closed once the X-ray source 100 is not operating and is then opened in connection with operating the X-ray source 100 to generate X-rays 10.

In an embodiment, the particle source 200 comprises a particle pre-accelerator 220. The pre-accelerator 220 is then arranged to accelerate solid and/or liquid µPs from the µP reservoir 210. Such a pre-acceleration is preferably conducted upstream of the µP acceleration as induced by the particle accelerator 250. Upstream and downstream as used herein relate to the direction of the particle stream 20, typically from the µP reservoir 210 towards the interaction region 1. The particle pre-accelerator 220 then induces a movement of the solid and/or liquid µPs towards the interaction region 1 and any additional devices or components of the µP source 200. In particular, a combination of the particle pre-accelerator 220 and the particle accelerator 250 is capable of generating a particle stream 20 of spatially separated and moving, solid and/or liquid µPs having a high average velocity at the interaction region 1.

The pre-acceleration of the µPs is advantageous since the µPs can thereby be accelerated prior to electrically charging and/or magnetizing the µPs. The pre-acceleration means that the density of the µPs in the particle stream 20 is reduced. A high density of, for instance, electrically charged µPs in the particle stream 20 may cause problems with space charge due to repelling µPs in the particle stream 20. However, pre-accelerating neutral µPs prior to electrically charging or magnetizing them imply that the density of the µPs at the point of charging or magnetization is reduced and any problems with repelling µPs and space charge and/or aggregation are thereby reduced.

Hence, in an embodiment, the µP source 200 comprises the µP reservoir 210 configured to comprise solid µP or a liquid. The µP source 200 also comprises the particle pre-accelerator 220 configured to accelerate the solid μPs and/or liquid μPs produced from the liquid.

The pre-accelerator 220 is, in an embodiment, configured to mechanically pre-accelerate the μPs from the μP reservoir 210 to form a particle stream 20 of spatially separated and moving, solid and/or liquid μPs. Such a pre-accelerator 220 could then move solid and/or liquid μPs from the μP reservoir 210 even if the solid μPs or the liquid therein is uncharged and not magnetic.

In an embodiment, the particle pre-accelerator 220 comprises a particle guide connected to the μP reservoir 210 and arranged relative to the μP reservoir 210 to enable a gravitational or centrifugal force acting on the solid μPs or liquid in the μP reservoir 210 to transfer solid and/or liquid μPs from the μP reservoir 210 and through the particle guide.

The particle guide may, in this embodiment, be in the form of, for instance, a tubing or nozzle connected to the μP reservoir 210 to enable solid μPs therein to move through the particle guide by means of a gravitational or centrifugal force. Correspondingly, if the μP reservoir 210 comprises a liquid, liquid μPs generated from the liquid could be moved, such as in the form of droplets, from the particle guide by means of a gravitational or centrifugal force. In an embodiment, the particle guide is arranged relative to the μP reservoir 210 so that gravitation acts on the μPs or liquid therein and causes them to move through an inlet/outlet in the μP reservoir 210 and through the particle guide. In another embodiment, the X-ray source 100 is arranged in a rotatable gantry, which will be further described herein. In such a case, rotation of the gantry and thereby of the X-ray source 100 arranged therein will expose the solid μPs or the liquid in the X-ray reservoir 210 to a centrifugal force that acts on the solid μPs or the liquid to move them from the X-ray source 210 and through the particle guide.

Figure 8:
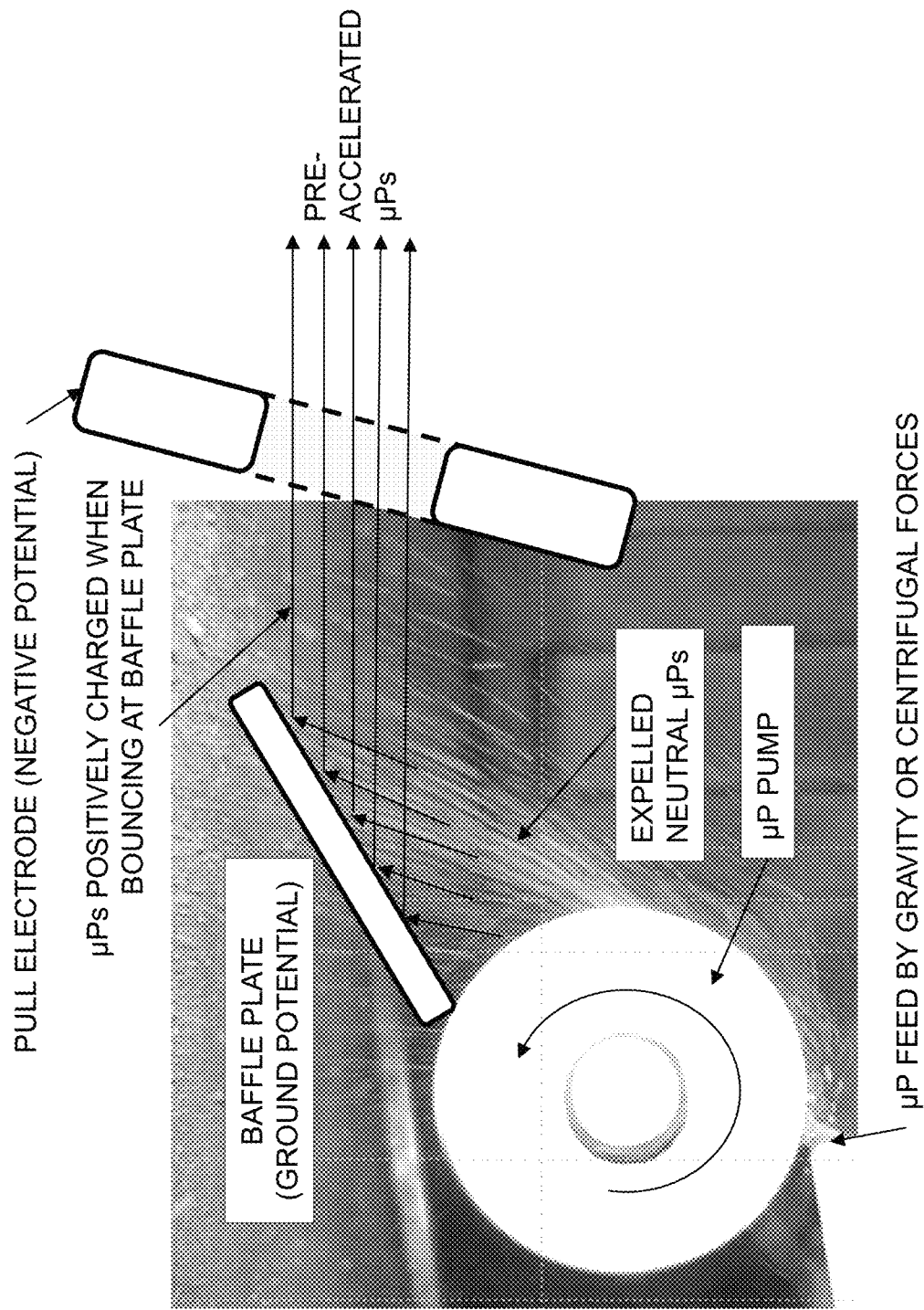
FIG. 8 is a schematic illustration of μP charging and feeding in an X-ray source according to another embodiment.

In an embodiment, the 220 pre-accelerator instead, or preferably additionally, comprises at least one μP pump configured to accelerate the solid and/or liquid μPs. The μP pump can be implemented according to various embodiments. In an embodiment, the μP pump comprises at least one rotating member having at least one envelope surface configured to engage incident μPs and transfer kinetic energy to the μPs. FIG. 8 schematically illustrates such an approach. μPs are, in this example, feed by gravitational or centrifugal forces through a particle guide attached to the μP reservoir 210. The μPs then incidence onto and engage a rotating member that mechanically accelerates the μPs forming a shower of accelerated μPs.

Experiments have shown that a simple rotating member may accelerate the μPs. However, the μPs tend to bounce from the outer surface of the rotating member thereby often experiencing only a single instance of momentum transfer. Consequently, μPs bouncing from a rotating member in the form of a simple smooth cylinder spill out in a large space angle and have a large span of velocities. A rough surface may provide for a more efficient acceleration of the μPs. Hence, it is preferred if the envelope or outer surface of the rotating member is rough, i.e., comprises surface structures.

Hence, in an embodiment, the at least one rotating member is at least one rotating cylinder. In a preferred embodiment, the at least one rotating cylinder has an envelope surface comprising surface structures. In another embodiment, the at least one rotating member is at least one rotor comprising at least one groove in an envelope surface of the at least one rotor.

A cylindrical rotor with a groove keeps the stream of μPs in the grove during acceleration. Additionally, the μPs are pushed in radial and tangential direction when the stream of μPs is directed towards the inner radius inside the groove. The μPs are kept in the groove for a while until they reach the outer radius of the rotor. As a consequence, the μPs experience mutual hits and wall contacts, which results in an efficient transfer of kinetic energy from the rotor into the μPs. The groove also prevents the μPs from escaping in an uncontrolled manner. The accelerated stream of μPs is thereby narrower and comprises μPs of a smaller span of velocities than with the rotating cylinder described above.

The at least one rotor may comprise a single groove or multiple grooves in its envelope or outer surface. For instance, the groove could have a spiral shape along the envelope surface.

It is also possible to use a particle pre-accelerator 220 comprising two rotating members preferably with grooves or two rotating cylinders arranged in vicinity of each other and rotating with opposite momenta of inertia. Such dual rotating members or cylinders may yield an even narrower stream of μPs as compared to using a single rotating member or cylinder.

Other examples of μP pumps could be used according to the embodiments to accelerate the μPs. These examples include, but are not limited to, a vibrator that shakes off μPs from the μP reservoir 210 and preferably into a vacuum chamber to be further described herein.

It is well known, see (Latham, 1995), that a plain liquid surface may develop protrusions upon the action of a high electric field. The electric force is then competing with surface tension. Primary normal modulation of the geometry, e.g., wave structures with slightly modulated electric field strength across the extension of the surface may exist. Such seed features may develop into sharp protrusions with enhanced electric field strength at their apexes. Latham calls this effect "field stripping". Highly charged droplets may detach, as the microscopic electric field is further enhanced. The process and the seed surface structure may be controlled by vibrating the surface and/or causing resonant vibration and geometrical modulation. The substrate may enable flexible shaping of the surface. The macroscopic electric field may be modulated either over time and/or space, synchronized or independently. Both, modulation of the surface geometry and modulation of the electrical field may be synchronized to yield a controlled production of liquid μPs and their acceleration. The produced μPs may be from an emulsion that comprises liquid and solid μPs.

Another example of a μP pump is a beam generator configured to generate an electron beam that irradiates layers of solid μPs and causes planar Coulomb explosion and fly-off of the solid μPs. The solid μPs are then accelerated from the μP reservoir 210 and are, in this example, additionally electrically charged by the electron beam. A further example of a μP pump is a laser source configured to irradiate a surface of solid μPs or a liquid in the μP reservoir 210 by laser causing micro-explosions to form solid and/or liquid μPs that are pre-accelerated by vapor pressure. Ferroelectric material, e.g., highly polarizable $BaTiO_3$, has shown to expel μPs upon interaction with plasma, see (Trottenberg et al., 2008), and may be used to produce a particle stream 20 of μPs. Negatively charged μPs may be produced by electron impact, e.g., in a scanning fashion, on a μP powder bed, an effect commonly called "smoking", see (Mahale, 2009) and (Eschey et al., 2009). Further examples of mechanical particle pre-accelerators that could be used are such pre-accelerators implemented substantially as the previously described mechanical particle accelerators.

The particle pre-accelerator 220 may accelerate the μPs by magnetic pre-acceleration instead of or as a complement to mechanical pre-acceleration.

In an embodiment, the μPs are magnetic, i.e., solid and/or liquid, magnetic μPs. For instance, the μPs could comprise a ferromagnetic material, a paramagnetic material and/or a diamagnetic material. In such a case, the particle pre-accelerator 220 comprises a magnetic particle pre-accelerator configured to generate a gradient magnetic field to accelerate the μPs.

The gradient magnetic field generated by the magnetic particle pre-accelerator thereby accelerates the μPs when exposed to the gradient magnetic field. The magnetic particle pre-accelerator may then generate the gradient magnetic field in a gap between at least two magnetic pole pairs. It is also, or alternatively, possible to have a magnetic particle pre-accelerator configured to generate a moving magnetic field, such as a rotating magnetic field. Such a rotating magnetic field will not only accelerate the μPs but may also cause the μPs to rotate. Rotating μPs improve heat dissipation of the μPs.

In an embodiment, the μPs are electrically charged, i.e., solid and/or liquid, electrically charged μPs. In such a case, the particle pre-accelerator 220 comprises an electric particle pre-accelerator configured to generate an electric field to accelerate the μPs. The electric particle pre-accelerator could be configured in a similar way to the previously described electric particle accelerator.

It is also possible to have a particle pre-accelerator 220 comprising a combination of two or more of a mechanical particle pre-accelerator, a magnetic particle pre-accelerator and an electric particle pre-accelerator.

In an embodiment, the μP source 200 comprises a particle charger 230 configured to electrically charge solid and/or liquid μPs into solid and/or liquid, electrically charged μPs. Charging of the μPs is preferably done prior to accelerating the μPs by the particle accelerator 250.

In a particular embodiment, the μP source 200 comprises the μP reservoir 210 configured to comprise solid μPs or a liquid. In such a particular embodiment, the particle charger 230 is configured to charge the solid μPs transferred from the μP reservoir 201 or liquid μPs produced from the liquid in the μP reservoir 210 into the solid and/or liquid, electrically charged μPs.

In an embodiment, the particle charger 230 comprises a first electrode plate, preferably at ground potential. The particle charger 230 also comprises a second electrode plate, charged with different potential to preferably generate an electric field, for instance in excess of 1 kV/mm. This electric field establishes a pulling electric field. The second electrode plate may be charged with negative voltage.

The second electrode plate may be arranged in vicinity of the first electrode plate and may comprise an aperture, see FIG. 8. Solid and/or liquid uncharged μPs engaging the first electrode plate become electrically charged to obtain solid and/or liquid, electrically charged μPs drawn by the electric field between the first electrode plate and the second electrode plate towards the second electrode plate and through the aperture.

In an embodiment, the first electrode plate is in the form of a stationary baffle plate as schematically shown in FIG. 8. In such a case, incoming neutral, i.e., uncharged, μPs bounce onto the baffle plate, such as after leaving a mechanical particle pre-accelerator. This stationary baffle plate then serves as a conductive base electrode for the second electrode plate at negative potential. The neutral μPs bounce elastically at the baffle plate and become positively charged during the impact on the baffle plate.

In a related embodiment, a moving baffle device, such as a rotating baffle device, could be used instead of a stationary baffle plate together with the second electrode plate. In such a case, the first electrode plate could be replaced by a rotating electric, preferably a rotating cylindrical electrode.

In an embodiment, the first electrode plate comprises at least one field enhancing feature to enhance the microscopic electric field, with respect to the macroscopic field, between the first electrode plate and the second electrode plate. Illustrative, but non-limiting, examples of such field enhancing features include a needle, a fin and a combination thereof. Alternatively, or in addition, the first electrode plate may comprise a dielectric that locally enhances the electric field at the point of charging of μPs.

In an embodiment, the particle charger 230 comprises an ion source configured to charge the μPs positively.

In an embodiment, the particle charger 230 comprises a plasma source configured to charge the μPs negatively. The plasma may be excited by an external RF electromagnetic field close to the first electrode plate.

Figure 5:
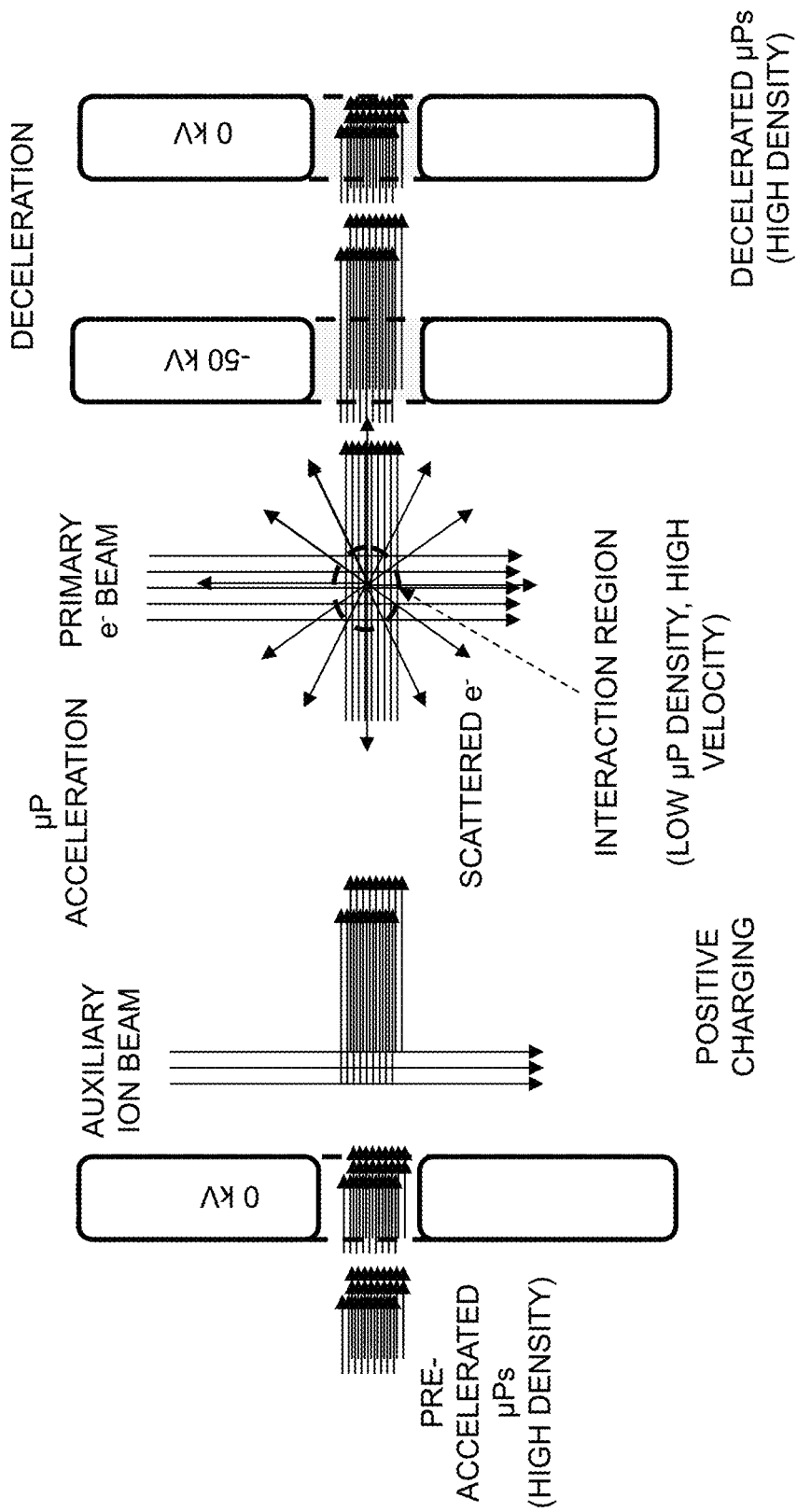
FIG. 5 is a schematic illustration of charge boosting, microparticle (μP) acceleration and deceleration in an X-ray source according to an embodiment.

In an embodiment, the particle charger 230 comprises a thermionic ionizer charger, see FIG. 5, to positively charge the μPs. For instance, heating tungsten with its work function of about 4.5 eV to more than 1800° C. may cause emission of electrons when the μPs are subject to an external electric field. Coating the μPs with material of lower work function like, for instance barium, may enable charging at lower temperatures. The charge gathered is limited by the electron-repelling electric field that the μPs generate upon positive charging. Thus, in practice, the positive charge accumulated nearly equals the charge gathered by a μP starting from a negatively charged electrode. The charge may be larger for elongated μPs than for spherical μPs. Heating μPs may cause thermionic ionization also in other parts of the X-ray source 100. This may help stabilizing uncontrolled negative charging of μPs, if any. μPs would then be neutralized or the polarity of their charge would even be reversed from negative to positive.

Figure 7:
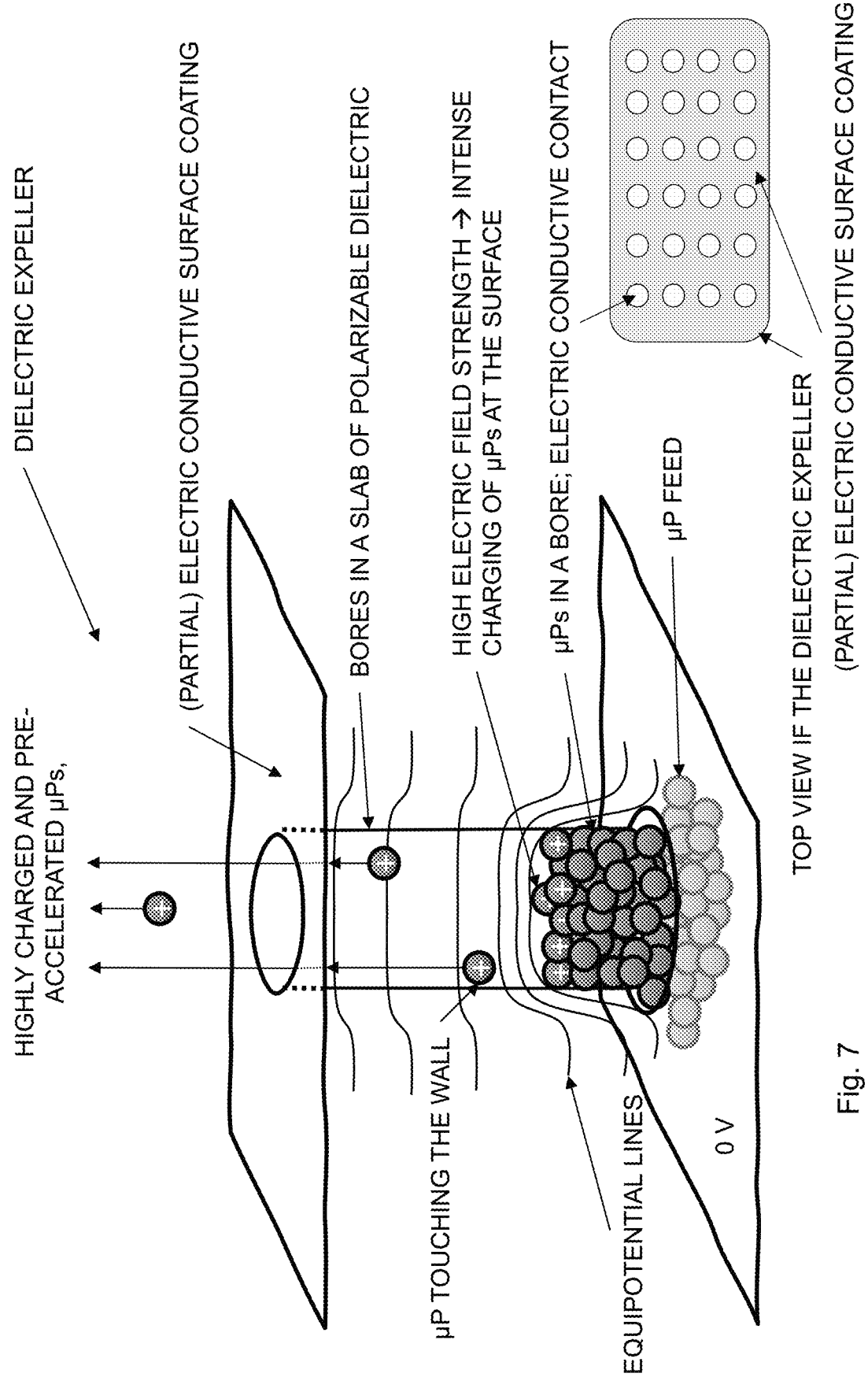
FIG. 7 is a schematic illustration of μP charging and feeding in an X-ray source according to an embodiment.

In an embodiment, the particle charger 230 comprises a dielectric expeller, see FIG. 7 or a combination of dielectric expeller and an electrode-based charger. A dielectric expeller that charges and expels μPs may be made of polarizable (dielectric) material that comprises bores or tunnels. μPs are fed, e.g., with high μP density, from the μP reservoir 210 through the tunnels into vacuum. An electric field may be generated by charging electrodes that, at least partially, cover the dielectric from either side. This structure serves as a dielectric expeller when exposed to an electric DC field or temporary modulated DC field, e.g., a high frequency field. At least one pair of metallic electrodes preferably covers the dielectric material and polarizes the dielectric when charged. The dielectric expeller may also function without electrodes on it by employing the electric field that it may be exposed to by extra electrodes that surround it and that, at least partially, have a distance to it. The bores in the dielectric material serve to expel electrically charged μPs from a μP feeding system into vacuum. Preferably the bores have a length that is larger than their diameter at the point where the μPs detach. Preferably, the electric field in the dielectric would be substantially directed along the bores when the bores were empty. When the bores are filled with μPs a radial electric field is dominating along the length of the bores, except where the top μPs in that row are located (top in vertical direction in FIG. 7). The electric field strength reaches a local maximum here. The μPs, marking the surface close to the open-end (opposite to the µP feed) will charge highly before detaching and losing electric conductive contact. µPs underneath, closer to the µP feed, will remain in electric conductive contact through the bores and deliver the electric charge, making sure that µP feed and µPs inside the bores share equal electric potential. With respect to the case when the bores were empty, the electric field at the apex of the µP filled columns is strongly enhanced. High electrical permittivity of the polarized dielectric material beneficially contributes. It may be preferred to use material of high polarizability, e.g., alumina or lithium niobate ($LiNbO_3$). The latter exhibits high permittivity of about 85. It may also be preferred to use partly conductive coating in the bores for those portions that ought to be filled with µPs in order to stabilize electrical contact and reduce abrasive effects.

The dielectric expeller may charge µPs with a charge of temporarily varying strength and even reversed polarity when subject to an electric field of varying strength and/or polarity.

In addition, piezoelectric expansion and shrinkage of dielectric material may serve to mechanically accelerate the µPs at the top of the µP columns, when the strength of the electric field in the dielectric expeller is modulated, e.g., by adding a high frequency component to the voltage between the electrodes.

It may also be beneficial to add lateral component(s) to the electric field in the dielectric charger to modulate the flux of µPs by the interplay of electric forces and forces of friction with the walls of the bores acting on the free and charged µPs. An additional rotating lateral electric field may serve to rotate µPs when they are traveling through the bores after detachment from the column of µPs and may touch the walls (see FIG. 7, µP touching the wall) before leaving into vacuum. In this way, torque may be transferred to spin µPs.

It is preferred to optimize the material with respect to dielectric, ferroelectric, piezoelectric characteristics as well as its mechanical properties like workability and hardness. Glass has proven its workability for laser-assisted drilling. It is preferred to select a material that withstands abrasive effects of the µPs.

The dielectric expeller constitutes a fast electrically controllable charger that may switch the particle stream 20. It may also imprint a direction of ejection of µPs and define size of sub-streams according to the size and length of the bores.

The dielectric expeller may comprise slanted bores in dielectric to eject µPs in the desired directions. The bores and polarizing electrodes on it may be grouped to expel charged µPs in groups depending on the control voltage applied to either group of electrodes and bores. In this way, the density and intrinsic structure of the generated particle stream 20 may be controlled.

In an embodiment, the particle charger 230 comprises a particle heater configured to heat the solid and/or liquid µPs to induce thermionic emission of electrons from the solid and/or liquid µPs to form solid and/or liquid, electrically charged µPs.

The particle charger 230 preferably also comprises an electron sink, e.g., a positively charged electrode, configured to collect electrons emitted from the heated solid and/or liquid, uncharged µPs.

In an embodiment, the strength of electrical charging, i.e. the amount of electric charge that the µPs carry on average may be modulated.

In an embodiment, the polarity of electrical charge that the µPs carry on average may over time be reversed by reversing the polarity of the charging of the charging means described above.

The charge Q of a spherical metallic µP of radius $r_{\mu P}$ sitting on a plane electrode subject to a macroscopic electric field $E_0$, that is locally enhanced by a field enhancement factor $\beta$ is given by:

$$Q = \frac{2}{3}\pi^3 \varepsilon_0 r_{\mu P}^2 \beta E_0 \qquad (3)$$

where $\varepsilon_0$ denotes the vacuum permittivity. The ratio of electric $F_E$ versus gravitational force Fg would be about $$\frac{F_E}{F_g} = \frac{1}{2g\rho_{\mu P}}\pi^2 \varepsilon_0 \beta E_0^2 \frac{1}{Gr_{\mu P}} \qquad (4)$$

where G denotes the enhancement of centrifugal force versus gravity (unity for simple gravitation), g denotes the acceleration of gravity at sea level at the equator. For most realistic ranges of $r_{\mu P}$, electrical forces $F_E$ dominate over gravitational forces $F_g$ on a µP with mass density $\rho_{\mu P}$, which is sitting on a horizontal plane subject to an electric field $E_0$. For example, $F_E/F_g=220$ for a voltage of 150 kV across a 2 cm wide plane gap ($\beta=1$).

Instead of, or as a complement to charging µPs, the µPs could be magnetized in a magnetic field in connection with or after they leave the µP reservoir 210 to enable a magnetic acceleration of the solid or liquid, magnetic µPs in a gradient magnetic field, which may comprise a rotary component.

In such an embodiment, the µP source 200 comprises a µP reservoir 210 configured to comprise solid µPs or a liquid. The µP source 200 also comprises a particle magnetizer 240 configured to magnetize solid µPs transferred from the µP reservoir 210 or liquid µPs produced from the liquid in the µP reservoir 210 into solid and/or liquid, magnetic µPs.

Figure 13:
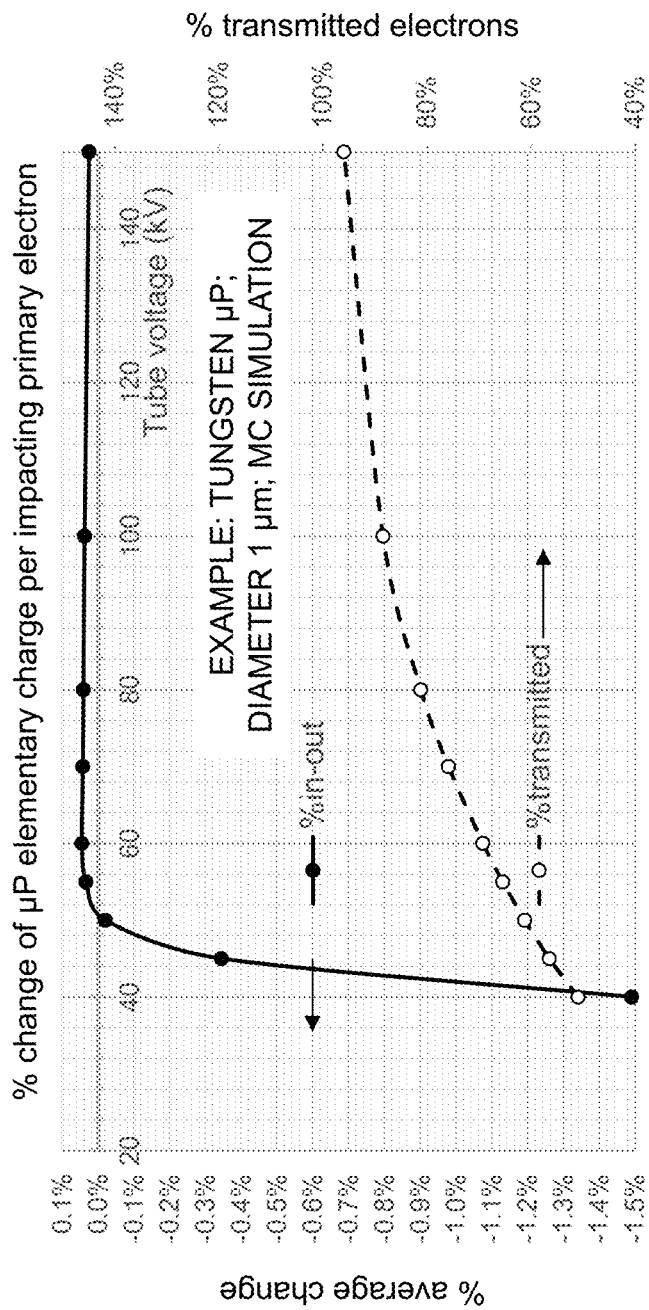
FIG. 13 illustrates the result of a Monte Carlo simulation of the charge balance of μPs at electron impact. The left vertical axis shows the simulated net charging of μPs during passage of the interaction region. Impacting electrons are assumed to have gained kinetic energy in an electron gun by passing the tube voltage indicated at the horizontal axis and may impact the μPs with that kinetic energy. The average electron transmission is presented at the right axis. As, on average, more electrons exit the μP than enter, it will gain positive charge for tube voltage beyond about 50 kV. It will alter its charge to the negative for much lower voltage. The potentials from space charge in the μP stream and the potential modulation due to absolute individual charge on a μP depend on the ambient electrode system and are ignored.

The µP source 200 comprises, in an embodiment, a particle discharger 260. Such a particle discharger 260 is then arranged to reduce adverse space charge effects and repelling forces among µPs. This may be preferred to optimally focus µPs and achieve a small cross section of the particle stream 20 in the interaction region 1. After acceleration and before entering the interaction region 1, the µPs may be at least partially discharged by such a particle discharger 260. High velocity is then already achieved and the µPs may not need to be charged anymore. Discharge may be achieved by interaction with agents of opposite polarity or charge state compared to the µPs. In case the µPs are initially electrically charged positive, a beam of electrons of relatively low energy may serve to, at least partially, discharge them. FIG. 13 shows that such electrons of energy below a threshold level may deliver negative net charge to the µPs, whereas high energy electrons tend to enhance the positive charge of such µPs. In case the µPs are initially intentionally charged negative, bombardment with positively charged ions may deliver positive charge and at least partially compensate the initial negative charge of the µPs. Charged µPs of different polarity that may recombine with initial µPs may also be used.

If magnetizable µPs are used, a high-frequency electromagnetic field with spatial gradient of the field strength may be applied by the particle de-charger 260. Alternatively, or additionally, the particle de-charger 260 may comprise means for pre-heating the magnetizable μPs to exceed their Curie temperature and at least partially erase their magnetic moments. This may serve to avoid unwanted aggregation of μPs.

After passing the interaction region 1, positively charged μPs may be sent through a particle de-charger 260 comprising an auxiliary electron beam. Negatively charged μP may be exposed to a high energy electron beam that generates an average scattered electron yield for the μPs in the particle stream 20 in excess of unity. Magnetizable μPs may be exposed to a high frequency magnetic field to de-magnetize them. Alternatively, they may be heated, e.g., by electron bombardment, to average temperatures beyond the Curie temperature.

Another means to compensate for space charge is setting the pressure of a neutral residual gas in the particle accelerator 250 high enough, e.g., up to 90% of the Paschen limit, to, at least partially, compensate for negative space charge in the particle stream 20 of at least partially negative charged μPs. The Paschen limit is given for a specific gas species as the product of pressure and distance between charged electrodes that enables a self-sustained gas discharge between these electrodes.

In an embodiment, the solid and/or liquid μPs are solid and/or liquid, electrically charged μPs. The X-ray source 100 then comprises a particle de-charger 260 arranged upstream and/or downstream of the interaction region 1 and configured to de-charge solid and/or liquid, electrically charged μPs.

In an embodiment, the particle source 200 comprises at least two electrodes at different potentials to generate a respective focusing electric field between two adjacent electrodes of the at least two electrodes. The respective focusing electric field is configured to, at least partially, balance repulsive forces in the particle stream 20 at the interaction region 1. The solid and/or liquid μPs are, in this embodiment, solid and/or liquid, electrically charged μPs.

Figure 9:
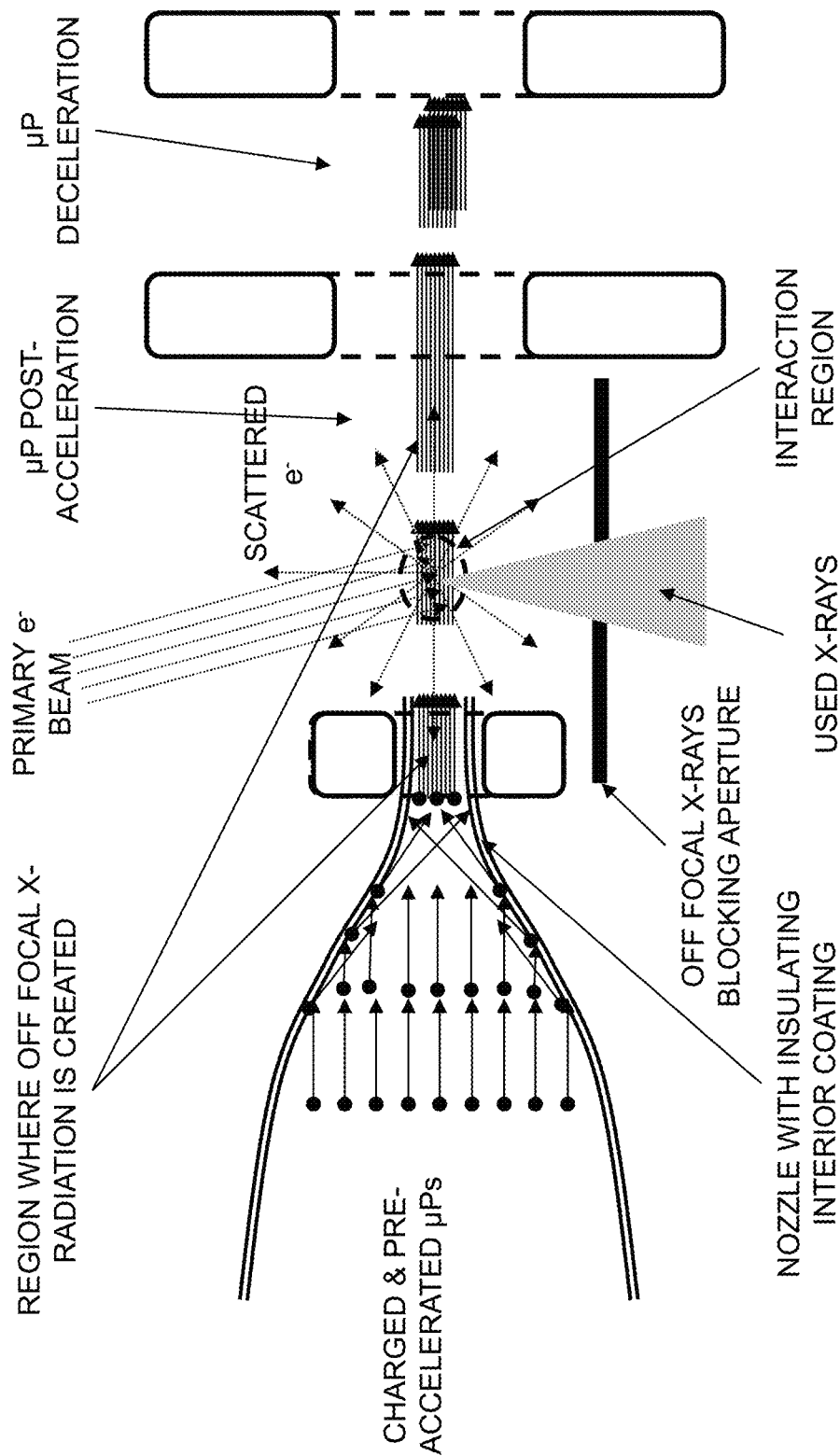
FIG. 9 is a schematic illustration of various embodiments for reducing off-focal radiation in an X-ray source according to an embodiment.

Off focal radiation (OFR) may be generated when solid and/or liquid μPs excited by electrons are scattered along the particle stream 20. The particle stream 20 is not opaque for X-rays 10. Electrons scatter in the interaction region 1 in all directions. Hence, an amount of off-focal radiation may emerge from the particle stream 20 downstream and upstream of the primary electron beam 30 as indicated in FIG. 9. As a consequence of such OFR, the focal volume may appear wider than the primary electron beam 30. This could have a negative impact on image resolution.

OFR may be blocked by having a blocking aperture positioned close to the particle stream 20. Desired X-rays 10 are then taken out through the aperture. Such an aperture may be subject to intense bombardment by scattered electrons and hot μPs and experience high thermal load. It is therefore preferred to apply cooling to such a blocking aperture. The distance of the focal region of the interaction region 1 to the aperture is preferably small, i.e., 10 cm or less, preferably 10 mm or less and more preferably 1 mm or less.

In an embodiment, the X-ray source 100 comprises an off-focal blocking element comprising an aperture arranged in vicinity of the interaction region 1. The off-focal blocking element is arranged to block off-focal X-rays generated at the interaction region 1 while passing focal X-rays 10 through the aperture.

It is generally preferred to have a thin particle stream 20, i.e., small stream diameter or thickness, to reduce off-focal radiation. In such a case, the electron flux along the particle stream 20 upstream or downstream of the interaction region 1 would then be minimal given the angular diffusion of scattered electrons. For instance, a nozzle positioned upstream of the interaction region 1 may focus the particle stream 20 and reduce its diameter to thereby suppress off-focal radiation, see FIGS. 9 and 10. In addition, or alternatively, a funnel may arranged downstream of the interaction region 1 to collect μPs after passing the interaction region 1 and thereby reduce the amount of off-focal radiation emitted along the used X-ray beam 10 due to interaction between these μPs and electrons scattered along the particle stream 20 downstream of the interaction region 1.

Figure 10:
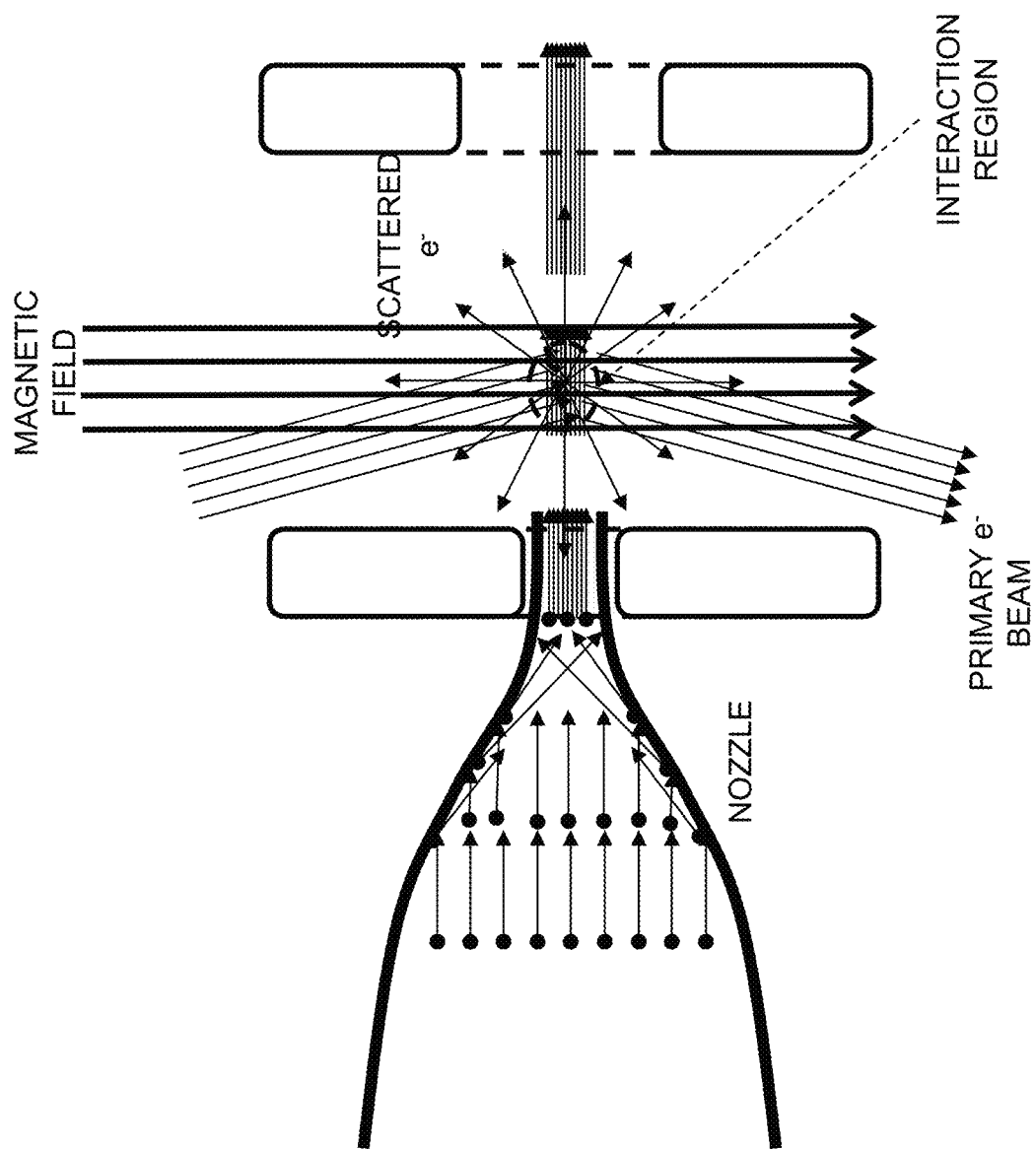
FIG. 10 is a schematic illustration of another embodiment for reducing off-focal radiation in an X-ray source according to an embodiment.

In an embodiment, the μPs may be guided by mechanical means, such as nozzle, which is schematically shown in FIGS. 9 and 10. Such a nozzle could then be arranged to focus the particle stream 20 in the interaction region 1 or anywhere else along the direction of the particle stream 20.

In an embodiment, the particle source 200 comprises a nozzle arranged upstream of the interaction region 1 and configured to focus the particle stream 20 at the interaction region 1.

In an embodiment, the interior of the nozzle with contact to the μPs may be of insulating material to preserve μP charge during wall contact. In another embodiment, the nozzle may be electrically conductive, such as metallic, and comprise an electrode for electrically charging μPs during exit. The nozzle may, for instance, be arranged as a baffle plate.

A magnetic field may be arranged across the interaction region 1 as shown in FIG. 10. In such a case, the magnetic field lines of the magnetic field are preferably directed normal to the particle stream 20. The magnetic field will then deflect scattered electrons travelling parallel with the particle stream 20 out from the particle stream 20. In fact, scattered electrons with a large component along the direction of the particle stream 20 will experience the largest deflection induced by the magnetic field out of the particle stream 20.

Hence, in an embodiment, the X-ray source 100 further comprises a magnetic source configured to provide or generate a magnetic field directed substantially perpendicular to the particle stream 20 and arranged to deflect electrons scattered in the interaction region 1 in a direction substantially parallel to the particle stream 20. This means that the magnetic field deflects these scattered electrons in a direction different than parallel with the particle stream 20.

An electric field may be applied along the particle stream 20 to further enhance the velocity of the μPs downstream of the interaction region 1 as shown in FIG. 9. This post-acceleration of μPs downstream of the interaction region 1 will reduce the μP density in the particle stream 20 downstream of the interaction region 1 as compared to the μP density in the particle stream 20 at the interaction region 1. As a consequence of this reduction in μP density, less interaction between scattered electrons and μPs take place downstream of the interaction region 1 and thereby less off-focal radiation is generated. The electric field may be shaped to expand the particle stream 20 and reduce its μP density downstream of the interaction region 1.

Hence, in an embodiment, the X-ray source 100 comprises a particle post-accelerator configured to provide an electric field downstream of the interaction region 1 to reduce a density of the solid and/or liquid μPs in the particle stream 20 downstream of the interaction region 1.

The μPs downstream of the interaction region 1 will carry high kinetic and thermal energy after impact of electrons in the interaction region 1. It may be advantageously to, for instance magnetically and/or electrically, decelerate the µPs before impact with any solid structures. For instance, the µPs may be directed through a system of electrodes that generates a repulsive electrical field to slow down the velocity of the µPs. This electrode system arranged downstream of the interaction region 1 is preferably charged more positive than any electrodes arranged upstream of the interaction region 1, such as forming part of the particle pre-accelerator 220 or the particle accelerator 250, see FIGS. 3-5.

In an embodiment, the X-ray source 100 further comprises a particle decelerator arranged downstream of the interaction region 1 and configured to decelerate and reduce a velocity of the solid and/or liquid µPs.

In an embodiment, the particle decelerator comprises a mechanical decelerator arranged to mechanically interact with the solid or liquid µPs to reduce a kinetic energy of the solid and/or liquid µPs. The mechanical decelerator could then operate as a mechanical braking system, which may be rotating, in a translational motion or stationary.

In another embodiment, the particle decelerator comprises an electrostatic decelerator comprising at least two electrodes arranged to provide a decelerating electric field configured to decelerate and reduce a velocity of the solid and/or liquid, electrically charged µPs.

In a further embodiment, the particle decelerator comprises a magnetic decelerator arranged to provide a gradient magnetic field configured to reduce a kinetic energy of the solid and/or liquid, magnetic µPs.

It is also possible to use a particle decelerator comprising a combination of at least two or all three of the mechanical decelerator, the electrostatic decelerator, and the magnetic decelerator.

A rough estimate of the input power per µP, supplied in the interaction region 1, reveals that for relevant use cases the parameter heat storage capacity of µPs governs a roughly linear temperature rise during interaction with an electron beam of up to 150 keV for µP velocities of 100 m/s and more.

The µP temperature is, firstly, controlled by the heat capacity and cross section of the µPs, and secondly, by tube voltage U, tube current/tube, focal spot length and width.

According to estimations, energy dissipation from µPs by heat radiation is expected to be relatively small for relevant cases and can usually by ignored, but the basic physics shall be described in this context. The intensity of black-body radiation $\dot{Q}$ from a spherical µP at temperature $T_0$ in an ambient environment of temperature $T_{ambient}$ is given by the Stephan-Boltzmann law to be $$\dot{Q} = \varepsilon \sigma A (T_0^4 - T_{ambient}^4) \tag{5}$$

where $\varepsilon$ is the emissivity of the surface, a the Stephan-Boltzmann constant, A the surface area of the µP. For $T_0 > 1000$ K and $T_{ambient} = 300$ K, the error in $\dot{Q}$ would be less than 1% when omitting the term $T_{ambient}$. Accordingly, the equation can be simplified into $$\dot{Q} \approx \varepsilon \sigma A\, T_0^4 \tag{6}$$

and the time for cooling t can be found by algebraic integration to be $$t \approx \frac{C}{3\varepsilon\sigma A}\left(\frac{1}{T_{final}^3} - \frac{1}{T_{hot}^3}\right) \tag{7}$$

where C is the heat capacity, $T_{final}$ is the temperature of the µP after cooling for a time t, and $T_{hot}$ is the initial temperature before cooling. A low particle density of µPs ensures that $T_{ambient}$ can be ignored and that isotropic temperature distribution within each µP and independence of $\varepsilon$ and C from temperature can be assumed. Nearfield effects enhancing the radiative coupling between µPs and electrodes are ignored at this point of the consideration. For steady state conditions for long heating times the equilibrium temperature $T_{steadystate}$ will be $$T_{staedystate} = \sqrt[4]{\frac{\dot{Q}}{\varepsilon \sigma A}}. \tag{8}$$

In an embodiment, the X-ray source 100 comprises a particle cooler arranged downstream of the interaction region 1. The particle cooler is then configured to cool the solid or liquid µPs.

In an embodiment, the particle cooler is a rotating member or drum arranged to dissipate heat and reduce the relative velocity of the µPs after leaving the interaction region 1. The rotating member or drum is preferably arranged on a liquid metal bearing, see (Behling, 2021), for thermal conductive cooling in addition to thermal radiative cooling. In another embodiment, at least one baffle plate may be arranged to slow down the µPs with the µPs impacting the baffle plate at a grazing angle. In a further embodiment, liquid metal could be used to capture the µPs and cool them. The µPs could be separated from the cooling liquid by a sieve and/or a centrifuge. It is also possible to combine these embodiments of the particle cooler. Moreover, liquid coated surfaces may serve to reduce unwanted pollution of the tube by uncontrolled µPs (particle getter).

The particle cooler is preferably arranged to dissipate the heat to an external heat exchanger outside of the vacuum frame of the X-ray source 100 that cools with a liquid or a gas and dissipates the heat to the ambient.

In an embodiment, a heat storage element could be included in the particle cooler and/or in the external heat exchanger to buffer peak heat input.

In an embodiment, the X-ray source 100 further comprises a µP collector arranged downstream of the interaction region 1 and configured to collect solid µPs or a liquid volume formed by liquid µPs.

In an embodiment, the µP source 200 comprises the previously mentioned µP reservoir 210. In this embodiment, the µP collector is connectable to the µP reservoir 210 via a particle transport system. The µP collector is then, preferably and in use, arranged relative to the µP reservoir 210 to transport the solid µPs or liquid from the µP collector through the particle transport system and to the µP reservoir 210 by gravity.

Figure 11B:
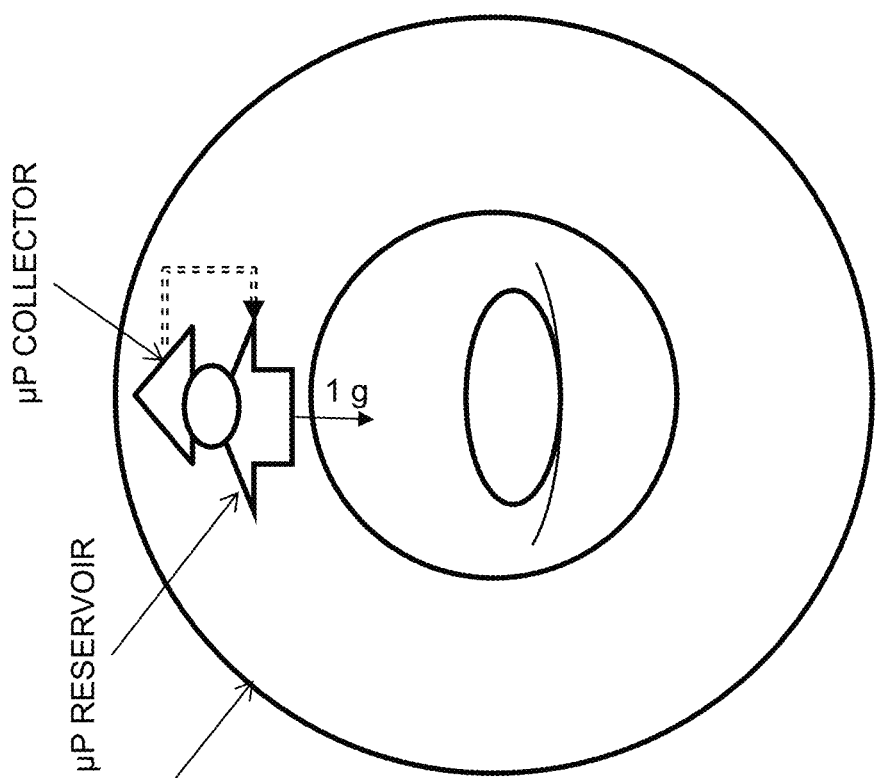
FIGS. 11A and 11B schematically illustrate an imaging system comprising an X-ray source according to an embodiment during μP reservoir emptying (11A) and μP reservoir reloading (11B).
Figure 11A:
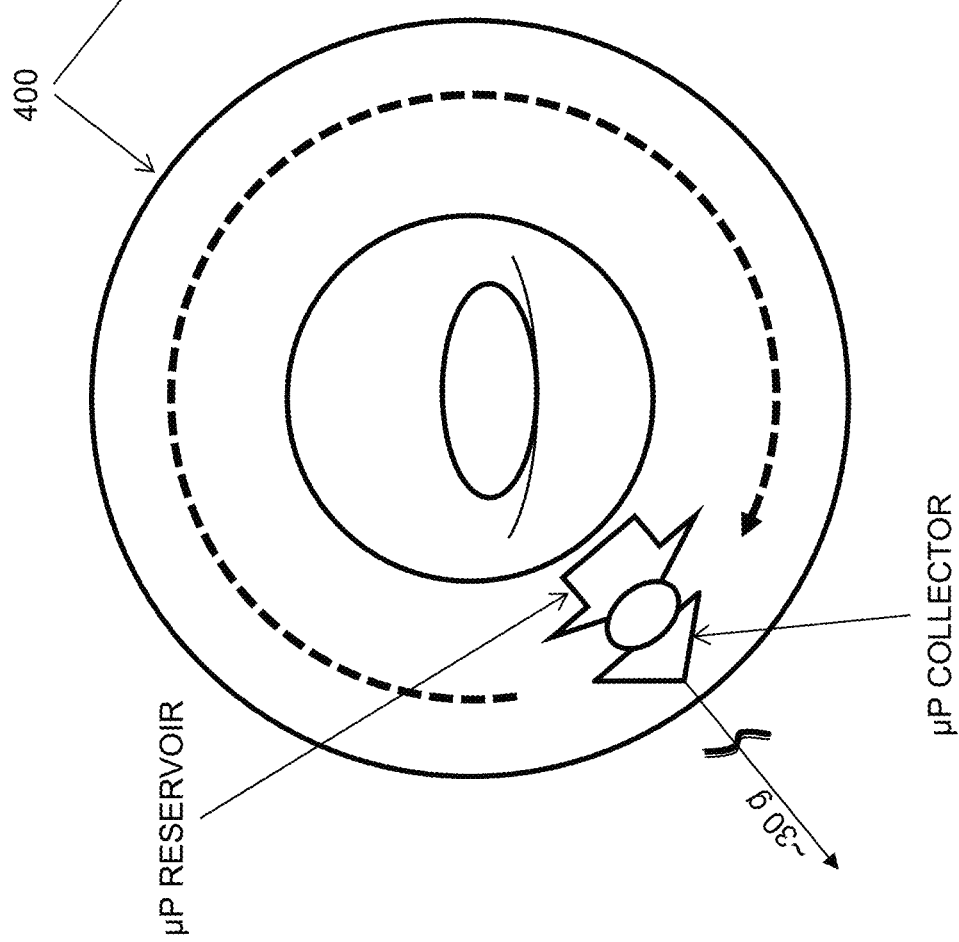

For instance, the X-ray source 100 may be arranged in a gantry, such as of a CT system, see FIGS. 11A and 11B. During operation, the µPs experience centrifugal acceleration and are collected in the µP collector preferably arranged at or in connection with the outer radius of the rotary gantry, see FIG. 10A. The centrifugal acceleration may reach 60 g for 300 rpm on a realistic gantry. This high value will help emptying the X-ray source 100 and collecting the µPs in the µP collector. It may be advised to support motion of the µPs towards the µP collector by vibration and/or by application short auxiliary high voltage pulses. After a CT scan, the gantry comes to rest with the X-ray source 100 at 12 hours position, see FIG. 10B. The force on the µPs reverses and gravity lets the µPs dripple down in a controlled way from the µP collector and through a particle transport system, such as in the form of a funnel and tubing, and into the µP reservoir 210. The µPs are stored in the µP reservoir 210, which is preferably mechanically shut when all collectable µPs have been gathered.

Figure 3:
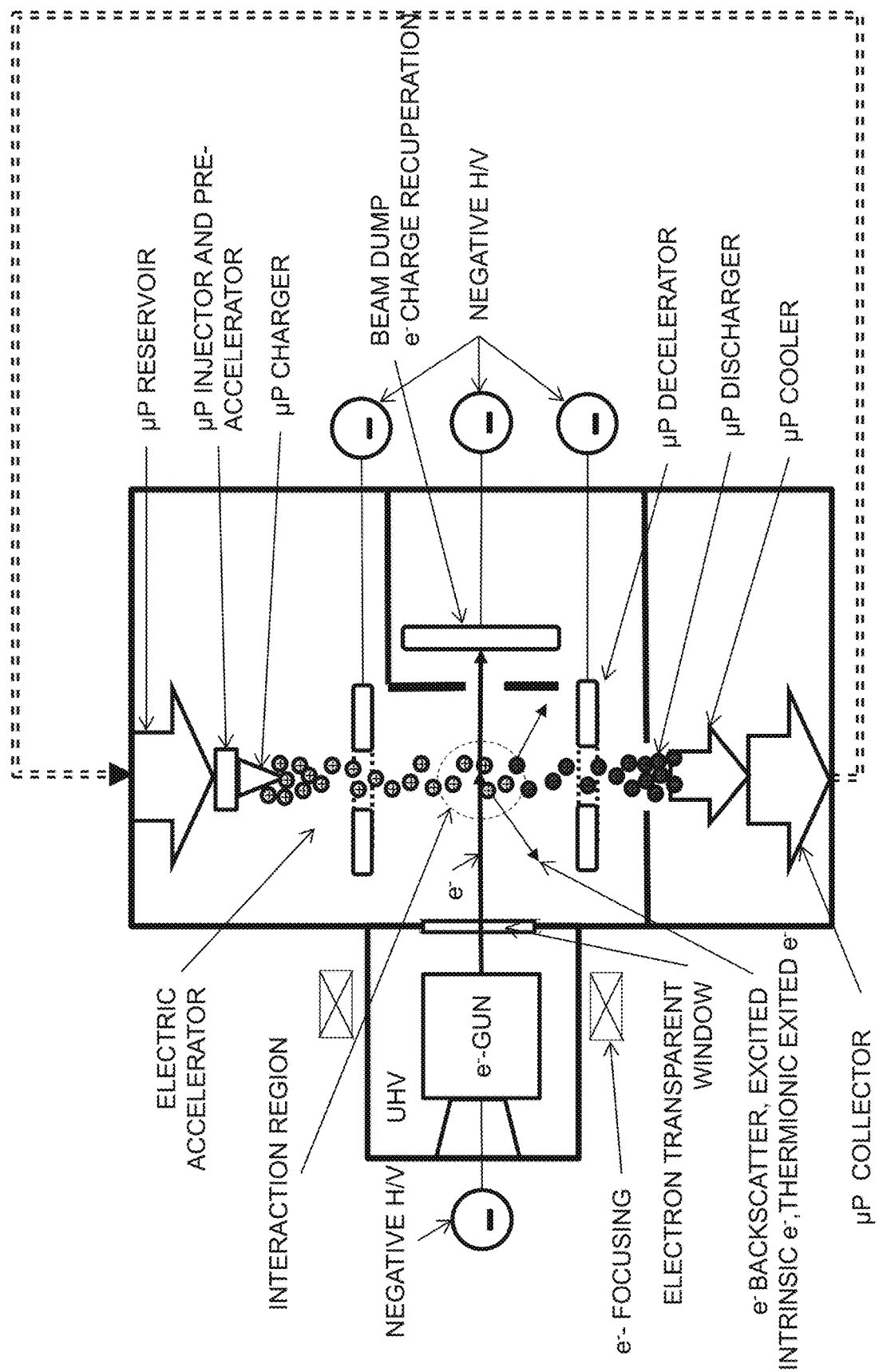
FIG. 3 is a schematic illustration of an X-ray source according to another embodiment.
Figure 4:
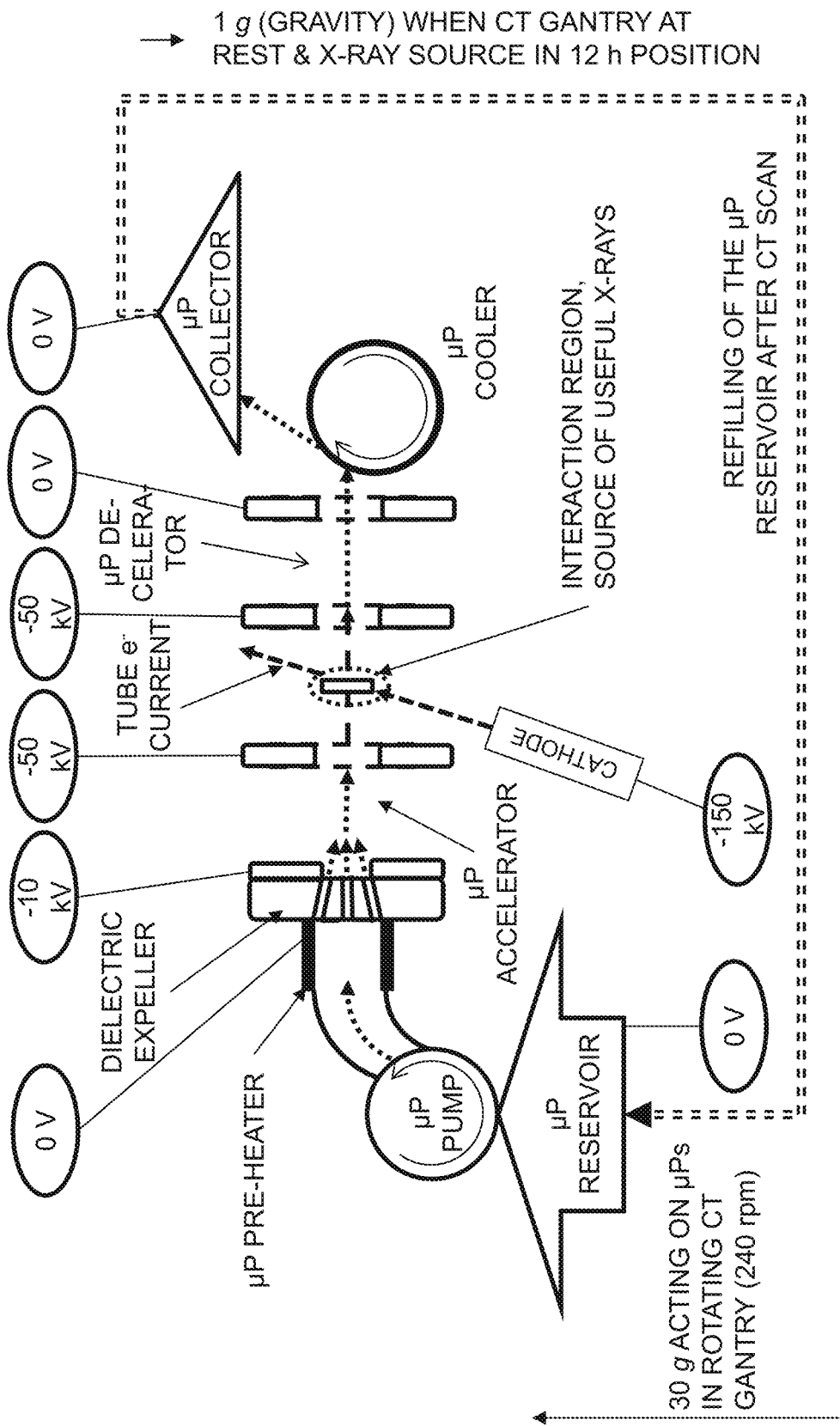
FIG. 4 is a schematic illustration of an X-ray source according to a further embodiment.

A µP transport system, see FIGS. 3 and 4, may be arranged to transfer collected µPs back to the µP reservoir 210. The µP transport may be arranged with support of gravity by re-positioning the X-ray source 100 such that µPs basically fall from the µP collector into the µP reservoir 210. For instance, if the X-ray source 100 is used in a CT system, the gantry of the CT system may be stopped after a CT scan or prior to a CT scan in a position that enables emptying the collector by, substantially, free fall, into the µP reservoir, see FIG. 11A for the X-ray source 100 in operation and FIG. 11B for the X-ray source 100 in idle state a CT system. This transfer process may in a similar way be applied for other X-ray systems.

Collection and transfer of µPs may be supported by a mechanical transfer system, e.g., by a piston, a conveyor belt or a wiper system or a combination. The transfer may be further supported by vibrating members of the X-ray source 100, on which the µPs will have gathered and to which they may stick, e.g., by Van der Waals forces or electric sticking forces at dielectric surfaces. These surfaces may also be subjected to electric fields, e.g., pulsed electric fields that detach µPs but are short enough to prevent the development of vacuum discharges. The pulses should preferably be short enough that loosened µPs are not substantially electrically accelerated and that µPs hit opposite electrodes elastically and not inelastically i.e., without causing damage or generation of plasma. Other means to clean surfaces may be plasma discharges to charge µPs negatively and detach them by generating a pulling electric field with a positively charged counter-electrode, see (Trottenberg et al., 2008). Similarly, instead of, or in addition to, a plasma cleaning procedure, an electron beam of relatively low average electron energy may be employed to scan surfaces and charge µPs negatively, e.g., and an electron beam with energy below 10 keV for tungsten µPs with more than 1 µm average diameter.

Before operating the X-ray source 100, the µPs may optionally be conditioned. Conditioning may comprise degassing by heating the µPs and the entire X-ray source 100 and high voltage conditioning while attached to a vacuum pump first, and later after pinch-off, i.e., closing the connection with the vacuum system. The X-ray source 100 may be operated for that purpose while attached to an external ultra-high vacuum pump. Hydrocarbon contamination of µPs and electrode surfaces may be removed by operating the X-ray source 100 in a wet hydrogen atmosphere. Oxide layers may be removed by partially flooding the tube with dry hydrogen gas and operating the X-ray source 100. Surfaces may be cleaned by plasma cleaning before assembly or after assembly in the X-ray source 100.

The X-ray source 100 may be conditioned to improve the high voltage stability by gradually increasing the high voltage between affected electrodes and supplying the electrodes with high voltage from a damped source, e.g., a source with resistive damping in series with the electrodes. It is preferred to avoid µP induced vacuum discharges (see (Latham, 1995). It is preferred to keep electric field strengths at negative electrodes by design to values smaller than 15 kV/mm, preferably smaller than 5 kV/mm.

After conditioning, the X-ray source 100 may be pinched off by closing the connection to the external vacuum pump. If the X-ray source 100 is to be operated as a so-called open tube or X-ray source 100, at least one vacuum pump remains attached. It is preferred to arrange the vacuum system such that the cathode region has the lowest residual gas pressure. If a single vacuum pump is used, other portions of the X-ray source 100 may be evacuated through apertures. An electron transparent window may be arranged between the cathode region of the X-ray source 100, i.e., the location of the electron source 300, and the interaction region 1, as described below. It is advised to keep the vacuum system free of µPs by, e.g., applying deflecting electric or magnetic fields or by mechanical means like sieves or rotary expellers.

The X-ray source 100 may comprise sensors for control. Sensors may be an X-ray output monitor, e.g., a photodiode system, a sensor of thermal radiation to measure the temperature and density of the particle stream 20, a Faraday cup current meter to sense the induced current through the µP energy recuperating electrode, a Faraday cup current meter for the electron induced current in an electron energy recuperating electrode, a µP scale, i.e., a sensor to measure the mass of µPs at a defined location for instance by sensing the frequency of resonant vibration of a member, and/or a µP counter, e.g., realized by a drift tube, and/or a laser driven light scattering sensor, see (Latham, 1995), section 7.3.2. Sub-µm sized µPs useful for medical imaging deliver typically too small a signal to be detected by laser driven light scattering sensors. It is then preferred to employ directly hit avalanche charge amplifiers that count the charge of individual µPs upon impact.

After passing the interaction region 1, electrons with a spectrum of charges and kinetic energies may be directed into at least a pair of charged electrodes, see FIG. 3. The power delivered by the charge from the electrons gathered in the electrode may be recuperated and fed back into the power supply. It may be advantageously to use multiple electrodes that charge to multiple voltages, e.g. depending on the residual kinetic energy and direction of electrons. Correspondingly, a beam dump may be arranged, in an embodiment, to collect electrons downstream of the interaction region 1 where the electrons still have a substantial average kinetic energy, see FIG. 3. Thus, the X-ray source 100 comprises, in an embodiment, a beam dump arranged downstream of the interaction region 1 and configured to collect electrons downstream of the interaction region 1.

In an embodiment, the X-ray source 100 comprises an electron charge recuperation member comprising at least two electrodes arranged downstream of the interaction region 1 and configured to collect a charge from electrons downstream of the interaction region 1. The X-ray source 100 also comprises a power supply connected to the µP source 200 and/or the electron source 300 and configured to supply power to the µP source 200 and/or the electron source 300. In such an embodiment, the electron charge recuperation member is connected to the power supply and configured to deliver, to the power supply, power generated based on the collected charge.

As for the electrons of the electron beam, also charged µPs with a spectrum of charges and kinetic energies may be directed into at least a pair of charged electrodes. The power delivered by the charge gathered in the electrode downstream of the interaction region 1 may be fed back into the power supply.

In an embodiment, the X-ray source 100 comprises a particle charge recuperation member comprising at least one electrode arranged downstream of the interaction region 1 and configured to collect a charge from solid and/or liquid, electrically charged µPs downstream of the interaction region 1. The X-ray source 100 also comprises, in this embodiment, a power supply connected to the µP source 200 and/or the electron source 300 and configured to supply power to the μP source 200 and/or the electron source 300. The particle charge recuperation member is then connected to the power supply and configured to supply, to the power supply, power generated based on the collected charge. A particle charge recuperation member may be implemented in the form of multiple electrodes that charge to multiple voltages, e.g., depending on charge state, residual kinetic energy and direction of the μPs. The particle charge recuperation member could then be implemented similar to electron beam dumps of, for instance, travelling wave tubes like klystrons.

The electron source 300 of the X-ray source 100 is preferably configured to generate an electron beam 30 of electrons having an average kinetic energy in the interaction region 1 of at least 1 keV, preferably at least 10 keV.

The electron accelerating voltage of the electron source 300 is, in an embodiment, adapted to the charging state of electrically charged μPs to compensate for their space charge potential and maintain a defined spectrum corresponding to the desired tube voltage. The tube voltage is defined for conventional tubes as the potential difference between the electron emitter and the anode and defines the spectrum. This relationship of stated tube voltage and spectrum is preferably maintained also for the electron source 300 of the invention.

In an embodiment, the electron source 300 produces multiple electron beams 30 of electrons that may intersect with the particle stream 20. As is further described herein, the μP source 200 could generate multiple particle streams 20. In such a case, the electron source 300 could produce the same number of electron beams 30 as particle streams 20 generated by the μP source 200. Each electron beam 30 may then intersect with one respective particle stream 20. It is, however, possible that at least two electron beams 30 intersect the same particle stream 20 in the interaction region 1. The multiple electron beams 30 could be of the same kinetic energy or different kinetic energies such that the same spectra of X-rays are generated or different spectra.

In an embodiment, electrons in the electron beam 30 produced by the electron source 300 may be deflected, e.g., by a magnetic field that points substantially in axial direction of the particle stream 20 to multiply pass the interaction region 1.

In an embodiment, electrons in the electron beam 30 produced by the electron source 300 may be deflected, e.g., by an electric field that points substantially in radial direction of the particle stream 20 to multiply pass the interaction region 1. The electric field may be supported by space charge of the particle stream 20.

In an embodiment, the current of the electron beam 30 may be switched off or current modulated, e.g., by applying a modulated repelling electric field between the electron emitter and at least one control electrode.

In an embodiment, the at least one electron emitter in the electron source 300 that produces the electrons in the electron beam 30 that intersects with the particle stream 20 may be a thermionic emitter, a field emitter or a combination thereof.

In an embodiment, the voltage of the electron source 300 is controlled in response to a signal that is representative of the density of the particle stream 20, preferably at the interaction region 1. Such a control of the accelerating voltage of the electron source 300 can balance the influence of μP induced space charge on the kinetic impact energy of electrons and the spectrum of the produced X-rays 10. The sensing may be replaced by simulation or prior calibration, e.g., using a look-up table.

In an embodiment, the electron cathode current of the electron source 300 is controlled in response to the desired X-ray output while considering the density of the particle stream 20, preferably at the interaction region 1.

It may be beneficial to separate the electron source 300 from the interaction region 1 to reduce the risk of polluting the cathode region, i.e., the electron source 300, with μPs. In such a case it may be preferred to separate the electron source 300 from the interaction region 1 by an electron transparent window. In such a case, the electron beam 30 traverses the electron transparent window, which is transparent for electrons but substantially intransparent for residual gas and μPs, before entering the interaction region 1. The thickness of the electron transparent window may depend on the desired tube voltage of the electron source 300 but is typically in the range of from 0.1 μm up to 10 μm, such as about 1 μm.

The electron transparent window may be made of various materials including, but not limited to, diamond and graphene.

The electron transparent window has the benefit of keeping the cathode region with the electron source 300 depleted of μPs, vapor, and/or residual gas that may be present in the interaction region 1. Electrodes in the cathode region typically bear the highest electrical field strength to generate a high current electron beam 30 at high kinetic energy (up to hundreds of kV). Hence, isolating the cathode region from μPs and residual gas minimizes the risk of uncontrolled high voltage discharge and breakdown. The electron transparent window is substantially tight for gas, vapor and μPs in the sense that it enables reduction of the gas pressure and/or the vapor pressure and/or the density of μPs in the cathode region by at least a factor of two, preferably by more than an order of magnitude, with respect to the interaction region 1. The electron transparent window may be supported by or comprise a grid structure.

In an embodiment, the X-ray source 100 comprises an electron transparent window separating the electron source 300 from the interaction region 1. The electron transparent window is transparent for electrons but substantially intransparent for residual gas, vapor and/or the solid and/or liquid μPs.

An additional advantage of the electron transparent window is that the μP anode of the invention could be combined with a gas target, such as a xenon (Xe) target. For instance, the solid and/or liquid μPs could be carried in a jet or stream of a gas, such as a Xe jet or stream. The electron transparent window would then separate vacuum in the cathode and Xe gas. In such an embodiment, neutral μPs could embedded in a jet or stream of gas, for instance, tungsten μPs embedded in a jet or stream of Xe gas.

In an embodiment, the microparticle source 200 is configured to generate the particle stream 20 of spatially separated and moving, solid and/or liquid microparticles embedded in a jet of a gas.

In an embodiment, the μP source 200 is configured to generate a particle stream 20 of spatially separated and moving, solid or liquid μPs having an average diameter selected within a range of from 0.05 μm up to 1 μm. For instance, spherical μPs of tungsten are commercially available from about 50 nm diameter. The diameter of the μPs may be adapted such that the backscattered electron yield is positive for all relevant tube voltages, such as for tube voltages of between 50 kV and 150 kV adapted for CT application. The average diameter of spherical tungsten μPs is preferably smaller than about 1 μm, see FIG. 12. For general medical radiography with a tube voltage range of between 40 kV and 150 kV, the average diameter is preferably below 0.8 μm.

The μPs are typically spherical μPs or nearly spherical μPs. However, the embodiments are not limited thereto. For instance, the μP may have an elongated shape, such that their length is larger than their diameter or width, such as two or more times larger than the diameter or width. This feature potentially enhances the electrical charge acquired by the particle charger 230 and/or the magnetic moment acquired by the particle magnetizer 240.

In an embodiment, the μP source 200 is configured to generate a particle stream 20 having, at the interaction region 1, an average diameter selected within a range of from 1 μm up to 1000 μm, preferably within a range of from 1 μm up to 100 μm, such as within a range of from 1 μm up to 10 μm.

In an embodiment, the μP source 200 is configured to generate a particle stream 20 of spatially separated and moving, solid and/or liquid tungsten μPs, preferably a particle stream 20 of spatially separated and moving, solid tungsten μPs, and more preferably a particle stream 20 of spatially separated and moving, solid and electrically charged tungsten μPs. Hence, in a preferred embodiment, the μPs are tungsten μPs.

The μPs in the particle stream 20 may be of the same μP species or different μP species. The particle stream 20 may, hence, be homogeneous or heterogeneous. The μPs may be solid μPs, liquid μPs or co-existing in liquid and solid phases, such as solid μPs coated with fluid, fluid contained in solid μPs, e.g., in a porous material. The μPs may also be solid sub-particles immersed in liquid or solid particles with a liquid core. Solid as used herein implies that the μPs are in solid form but do not necessarily have to be uniform or solid in terms of non-porous. Hence, also at least partly porous, solid μPs could be used according to the invention. The μPs may comprise electric conductive, non-conductive, semi-conductive material or a combination thereof, e.g., dielectric, that is at least partly coated with conductive material or conductive material embedded in a dielectric. The μPs may have ferroelectric characteristics and high polarizability that may support charging while a solid sub-component of the μPs may be of high-Z material to enhance the output of X-rays in the interaction region 1. The μPs may be magnetizable, ferromagnetic, diamagnetic, or paramagnetic. The μPs may be hollow to minimize their mass while maximizing their (surface) charge and, hence, their velocity in the interaction region 1. The μPs may change their state of phase during the movement through the X-ray source 100.

Advantageously, the μPs may comprise a combination of a liquid metal of low meting temperature and a solid component of high melting temperature, e.g., GaInSn and tungsten, or an alternative liquid-solid combination. Ga-based liquid metal has proven its compatibility with ultra-high vacuum application even at elevated temperature of a few hundred degrees centigrade. Attached to refractory metals like W, Mo, and Ta the Ga-based metal forms a moderate chemical-physical bonding without totally dissolving the solid component. Ga-based liquid has limited chemical reactivity with solid refractory metals in relevant temperature range, e.g., below 500° C. That enables co-existence and non-zero contact angle, i.e., the liquid attaches to the solid without dissolving it. Other metals, e.g., aluminum, iron or copper will chemically react so intense that the solid and the liquid may form eutectic at relevant temperatures and reaction times. This would irreversibly destroy the nature of the μPs and would render recycling of μPs after passage of the interaction region difficult. The refractory metals, referenced above, however, may keep their composition. A solid component like tungsten with its large atomic number and material density will, beneficially, enhance the X-ray conversion in comparison with non-refractory metals and, Ga-based liquid metal.

When exposed to a pulling electric field, the liquid may serve to improve electrical charging when it maintains electric conductive contact during charging and prior to μP detachment from a charging electrode, as indicated in FIG. 7. The liquid component may also serve as a "glue" to enhance sticking force with collection devices to prevent μPs from uncontrolled pollution of the vacuum chamber and ignition of vacuum discharges, as pointed out above.

To use meltable metal that is solid at room temperature, it may be advised to partially melt the μPs and enhance their temperature. This may be helpful when an elongated liquid conductive contact may be maintained during charging. Adjusting the temperature of μPs appropriately may help balancing temperature-dependent characteristics, e.g., polarizability, conductivity, thermionic emissivity of electrons. It may also help monitoring the particle stream 20 by sensing thermal radiation.

A temperature control element for heating and/or cooling the μP material may be used to adjust the temperature of the μPs before they enter the interaction region 1. Elongated μPs acquire higher charge in contact with an electrode when subject to an electric field than spherical μPs, see (Latham, 1995). It will be beneficial to maintain electric conductive contact when a μP is about to detach under electric force. By capillary forces, liquid metal, that may be molten in the temperature control element, may help charging. The liquid metal may establish a filamentary "necked" electric conductive connection between charging electrode and the apex of a μP. This will enhance the local electric field at the apex and, thus, the acquired charge of the μPs. Moreover, liquid may form sharp protrusions under the action of an electric field. Such protrusions also enhance the local electric field and, thus, the charge that a μP carries after detachment, as described above. Detachment of spherical, and also such elongated features may be supported by vibrating or shaking laterally or longitudinally the electrode or the nozzle of a metal jet from which the liquid droplets may be produced. Generally, a high charge state will be beneficial for acceleration. Employing moderate electric field strength for acceleration will allow limiting the voltage between the electrodes in the particle accelerator 250, and improve the electrical stability, by avoiding vacuum discharges. The optional temperature control element may, for instance, employ heat radiation heating and cooling, convective heating and cooling during contact with a baffle plate or a mechanical μP pump, electromagnetic heating in an R/F field, and laser heating.

Currently preferred μPs are homogeneous solid μPs of tungsten with a size in the order of half a micrometer in diameter. These are commercially available, produce relatively low vapor pressure at relevant temperatures and offer the benefit of a relatively high atomic number.

Various temporal characteristics of the X-ray source 100 of the invention may be employed. The particle stream 20 of μPs may be continuous for the entire duration of an X-ray exposure or a series of X-ray exposures, e.g., until the μP reservoir 210 has emptied. It may be beneficial for specific applications to operate bunches of μPs. The particle stream 20 may then consist of bunches, each comprising a limited and defined number of µPs. The flux of µPs passing the interaction region 1 may be modulated, e.g., to modulate the X-ray output.

The µPs may pass a quality selection element that selects µPs for optimal characteristics, e.g., according to charge state, mass, size, magnetization, velocity, before being accelerated and entering the interaction region 1. Such a quality selection element may comprise an electric field pointing orthogonal to the main axis of the particle stream 20, and/or a magnetic field pointing orthogonal to employ Lorentz force for selection. The quality selection element may employ gravity and/or centrifugal force. It may mechanically change the pathway of µPs upon measuring the average momentum transferred when µPs may be bouncing. In an embodiment, the quality selection element may comprise a sieve. In an embodiment, the quality selection element may comprise an aperture, through which µPs of the desired quality enter the next stage of processing, such as charging, magnetization or acceleration. Such a quality selection element may be placed in the particle stream 20 wherever necessary.

Figure 14:
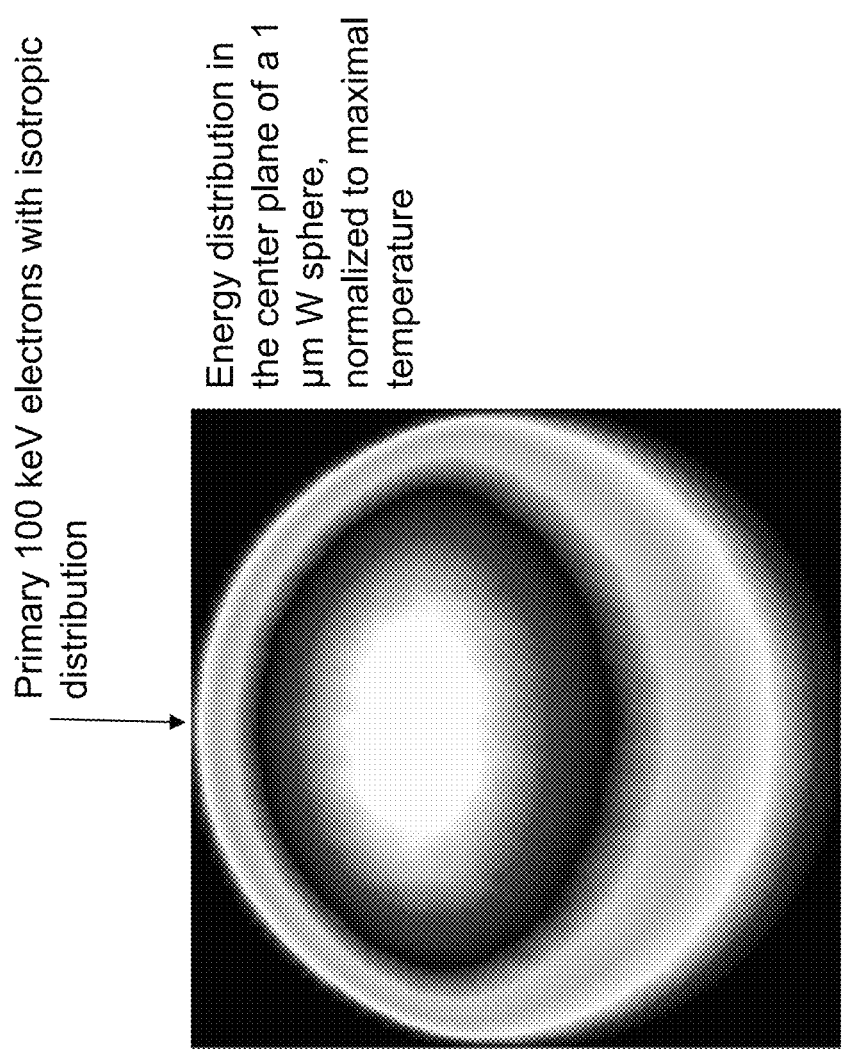
FIG. 14 schematically depicts the simulated temperature distribution of a tungsten μP in its central cross-sectional area. The μP heats up slightly non-isotopically upon bombardment with electrons of 100 keV kinetic energy, which are assumed to impinge on the μP with constant current density in space. The temperature distribution is coded in grey shadows. The maximum temperature appears slightly above the middle line in the picture, black color at the perimeter corresponds to ambient temperature.

It may be beneficial to rotate µPs in the particle stream 20. Given the limited travel length of electrons in matter, rotation about an axis along the direction of the particle stream 20 will help homogenizing their internal temperature gained in the interaction region 1, see FIG. 14. Preferably, momenta of inertia are substantially parallel with the direction of motion in the particle stream 20. Rotation may also stabilize the motion of µPs by gyroscopic moments. Torque may be transferred by bouncing of µPs under grazing impact from a baffle plate or sending the µPs through a rotating magnetic field.

In an embodiment, the µP source 200 is configured to generate a particle stream 20 of spatially separated and moving, solid and/or liquid, µPs comprising microstructures.

In an embodiment, the microstructures are selected from at least one of electrically conductive microstructures, layered microstructures, microstructures having a peripheral mechanically hard portion, microstructures having a peripheral mechanically ductile portion, sintered microstructures, electrically polarizable microstructures, and magnetizable microstructures.

In an embodiment, the µP source 200 is configured to generate a particle stream 20 of spatially separated and moving, solid µPs. In a particular embodiment, the µP source 200 is configured to generate a particle stream 20 of spatially separated and moving, solid and electrically charged µPs. In another particular embodiment, the µP source 200 is configured to generate a particle stream 20 of spatially separated and moving, solid, electrically charged and magnetic µPs.

In an embodiment, the X-ray source 200 comprises a vacuum chamber. In such an embodiment, the µP source 200 is configured to produce the particle stream 20 of solid and/or liquid µPs moving inside the vacuum chamber and the electron source 300 is configured to produce the electron beam 30 incident onto the particle stream 20 at the interaction region 1 inside the vacuum chamber.

The shape and the dimension of the interaction region 1 defines imaging characteristics, such as spatial resolution achievable in the central beam of used X-rays, i.e., in the center, and at the periphery of the image, and OFR. The thickness of the particle stream 20 defines the axial dimension of the focal spot or volume.

The width of the focal volume is defined by the smallest dimension of the electron beam 30 and particle stream 20 in the interaction region 1. In order to minimize the µP material flow and to make optimal use of the electron beam 30, both should preferably have equal dimensions. OFR is then minimized as well.

As the particle stream 20 is highly transparent for X-rays 10, they can be taken out in longitudinal direction of the particle stream 20, other than for reflection targets and transparent targets. This may enable novel modes of operation with "focal volume" characteristics different from conventional targets. X-rays 10 may e.g., be taken out in longitudinal direction of the particle stream 20. By employing materials, such as carbon or beryllium, electrodes and the frame of the X-ray source 100 may be arranged to be substantially transparent for the used X-rays to yield a desired fan of X-rays.

The µPs of the particle stream 20 travel through the interaction region 1. At least one electron beam 30 of energized electrons travels in substantially orthogonal direction to the particle stream 20. The electrons excite the µPs to create X-rays 10 upon interaction with the µPs. The spatial density of the µPs in the interaction region 1 is high enough to have a substantial portion of electrons interacting with the µPs such that a substantial useful flux of X-rays 10 emerges from the interaction region 1.

As was mentioned in the foregoing, it is possible to have multiple particle streams 20 coming from different directions and that interact with electrons in the interaction region 1. Hence, in an embodiment, the µP source 200 is configured to generate multiple particle streams 20 of spatially separated and moving, solid and/or liquid µPs. These multiple particle streams 20 may be arranged parallel with each other or have a non-zero angle with each other. They may have different angles of incidence in the interaction region 1. They may intersect with each other, e.g., in the interaction region 1 to enhance the µP density while minimizing effects of expansion from space charge. The electron source 300 is then configured to generate the electron beam 30 of electrons incident onto the multiple particle streams 20 in the interaction region 1 to excite solid and/or liquid µPs in the interaction region 1 to generate X-rays 10. Alternatively, the electron source 300 could generate multiple electron beams 30 incident onto the different particle streams 20 in the interaction region 1.

Multiple particle streams 20 may, for instance, be employed in parallel to generate a grid-like X-ray source. This concept would, moreover, enable fast switching between sub-sources of a chain of sources by electron deflection. Exciting electrons may be sent to one or the other particle stream 20 to generate a time series of different X-ray projections.

In an embodiment, the multiple particle streams 20 comprise µPs having different average sizes. Such multiple particle streams 20 of differently sized µPs may then be used in a layered fashion. As electrons are scattered by the first interaction with a µP in the top layer close to the electron source 300 and lose some energy, it may be beneficial to have smaller µPs interacting in the lower region further away from the electron source 300 since otherwise sloweddown electrons may alter the charge of these µPs, which may be undesired.

However, if the power density in the interaction region 1 is high, it may be beneficial to have a first interaction layer comprised by the smallest µPs since they have the highest speed, cool best by thermal radiation and scatter electrons the least. Larger µPs may then be used at the bottom layer to maximize the overall conversion efficiency. The various alternatives may apply depending on the tube voltage.

Top and bottom layer as used herein refers to μPs in the multiple particle streams 20 as seen from the electron source 300. Hence, the top layer μPs are μPs of the particle stream 20 closest to the electron source 300 among the multiple particle streams 20, whereas the bottom layer μPs are μPs of the particle stream 20 furthest away from the electron source 300 among the multiple particle streams 20.

In an embodiment, the μP source 200 is configured to generate at least a first particle stream of spatially separated and moving, solid and/or liquid μPs having a first average diameter of the μPs and a second particle stream of spatially separated and moving, solid and/or liquid μPs having a second, different average diameter of the μPs. In such an embodiment, the electron source 300 is configured to generate the electron beam 30 of electrons incident onto the first particle stream followed by the second particle stream in the interaction region 1.

In a particular embodiment, the first average diameter is larger than the second average diameter. In another particular embodiment, the second average diameter is larger than the first average diameter. The present X-ray source 100 for production of X-ray brake radiation employs a particle stream 20 of extremely fast moving separated solid μPs or droplets of liquid. Energized electrons, accelerated in a gap between high voltage electrodes, interact with the fast moving μPs to generate X-rays 10. The μPs are preferably electrically charged and/or magnetized, electromagnetically accelerated and then exposed to an electron beam 30 and eventually cooled and captured. The initial net charge, acquired during the optional, but preferred charging operation is preferably substantially maintained during interaction with the energized electrons. Fortunately, the scattered electron yield for μm sized μPs is close to unity for excitation with tens of keV electrons, see FIG. 12. However, μPs under bombardment of slowed-down electrons in the cloud of scattered electrons may preferably be filtered out, e.g., by electrostatic means.

The dwell time of the μPs under electron impact is preferably low. Realistic and suitable conditions of μP size, electron impact energy and μP velocity allow the permitted power density at interaction to be superior to other X-ray target technologies. It is expected that the heat capacity of the μPs in a realistic range of sizes is large enough and the dwell time under electron impact sufficiently short to yield a low enough vapor pressure that allows for frequent recycling of the μPs, e.g., by re-filling the microparticle reservoir 210.

The density of μPs is inversely proportional to their velocity. A minimal density is required to have electrons interact with material of at least an equivalent integrated thickness of a few micrometers for tube voltages of about 100 kV and acceptable conversion efficiency. Sufficient initial μP supply could be achieved, for instance, by a combination of pre-acceleration and acceleration.

Advantageously, the particle stream 20 should have minimal dimension in the region of interaction with electrons, i.e., the interaction region 1. This may be achieved, for instance, by focusing the μPs. For instance, a wide stream of μPs may leave the μP reservoir 210 and then concentrate at the interaction region 1, e.g., by convex shaping the positive electrode, and widen at the exit to simplify cooling and gathering. It would be beneficial to restrict the particle density to avoid collisions.

The main portion of the acceleration of μPs is preferably electrostatic. However, it may also be electromagnetic, e.g., by a travelling electric field. The travelling electric field is then preferably synchronized with the velocity of the μPs. Magnetic acceleration could be used but is typically less efficient due to the low Curie temperature of most materials with high permanent magnetic moment. Hence, in a preferred embodiment, the μP acceleration is an electrostatic acceleration.

The preferred electrical charge of the μPs enables electric μP acceleration. Given a high enough local field enhancement factor β, a gap voltage in the order of 150 kV may drive the velocity of sub-micrometer μPs to more than 1000 m/s or even a mile per second. The strength and size of the electric field can be adjusted such that the μPs are focused when they enter the interaction region 1. An additional rotating magnetic field may rotate the μPs for better heat dissipation or to employ gyroscopic effects fighting gravitational deflection.

For simplicity of the high voltage supply, the voltage for acceleration of electrically charged μPs may be the same as the tube voltage, i.e., the voltage for the electron source 300. However, voltage for acceleration of μPs can also be lower than the tube voltage to avoid high voltage vacuum discharges.

After X-ray production the heated μPs preferably enter pairs of electrodes for electrostatic deceleration, and elements for cooling and collection. The μPs should preferably impact electrodes at velocities below the limit of inelastic collision to prevent damaging impact. Charge may partially be recuperated.

Another aspect of the invention relates to an X-ray system 400, see FIGS. 11A and 11B, comprising an X-ray source 100 according to invention.

In an embodiment, such an X-ray system 400 may be a CT system, a medical radiographic system, an X-ray diffraction or X-ray fluorescence system, a dark-field imaging system, an X-ray irradiation system or an X-ray pulse generator or another system utilizing X-rays.

An advantage of the X-ray source 100 is that it does not essentially require any active pumping. The X-ray source 100 is therefore compatible with medical CT applications, where the X-ray source 100 rotates with high angular speed of up to five rounds per second on a CT gantry. The X-ray source 100 facilitates, due to the absence of a heavy anode of conventional X-ray targets, angular gantry velocities beyond 300 rpm. Such high velocities facilitate transportation of μPs from the μP reservoir to the μP collector, see FIG. 11A.

The μP reservoir 210 comprising the μPs or liquid to be formed into liquid μPs will rotate during scanning around an object and thereby experiences up to, for instance, 30 g or even 60 g centrifugal acceleration. The centrifugal force pressurizes the μPs in the μP reservoir 210. When the CT system is about to create X-rays, at least a relevant portion of μPs will travel along an S-shaped trajectory as indicated in FIG. 4. Advantageously, the particle stream 20 in the interaction region 1 will be flowing tangential to the rotating CT gantry to allow for homogeneous X-ray illumination of the X-ray detector of the CT system 400. This is further enabled by the fact that electric forces typically dominate, as shown above. Other X-ray imaging systems may operate accordingly.

Illustrative, but non-limiting, supply voltages for the various electrodes of the X-ray source 100 are shown in FIG. 4. FIG. 4 roughly indicates the distribution of high voltage potentials. In this example, the μPs are charged positively by a dielectric expeller. For infinitely low μP charge, the space charge potential of the particle stream 20 and the additional potential modulation by the individual μPs can be ignored. In this approximation, the μPs are hit in the interaction region 1 by electrons of 100 keV kinetic energy, corresponding to a tube voltage of 100 kV. The tube voltage is defined as the difference of the potential of the electron emitter in the cathode (−150 kV) and the individual μPs in the particle stream 20 (−50 kV) travelling through the interaction region 1. The potential in the interaction region 1 is defined by the adjacent electrodes that closely surround the particle stream 20. The electric field in the interaction region 1 is nearly vanishing.

In an embodiment, the μPs leave the μP reservoir 210 radially in relation to the CT gantry and are diverted into a tangential track, e.g. by a mechanical pre-accelerator like a rotating pump or a baffle plate and/or a curved diverter or nozzle, as indicated in FIG. 4. After optional but preferred positive charging in a μP expeller acting as particle charger 230, the μPs are electrically accelerated primarily in tangential direction of the CT gantry by the particle accelerator 250. The particle stream 20 of μPs interacts with the axial electron beam 30, which comes in normal to the particle stream 20 along the axial direction of the CT gantry. The μPs leave the interaction region 1 and describe a curved outward trajectory during electrical deceleration and cooling, e.g., by a rotating drum, as indicated in FIG. 4. When centrifugal forces exceed electrical forces downstream of the decelerator, i.e., in a field-less region, the gantry rotation helps collecting the irradiated μPs in the μP collector at the outer portion of the CT gantry, see also FIGS. 11A and 11B.

After finishing a CT scan, the CT gantry beneficially comes to rest with the X-ray source 100 in the 12 hours top position, see FIG. 11B. Centrifugal force is thereby superseded by gravitation. Electric supply of electrodes may be switched off such that gravitational forces dominate. The collected μPs may drip down and gather again in the μP reservoir 210. After collecting the μPs, which may be supported by vibrating the μP collector or electrical detachment from walls by auxiliary electrodes (not shown in FIG. 4), the μP reservoir 210 is closed, e.g., by a lid or other means to prepare for the next CT scan. The μP reservoir 210 constitutes a storage device, which is emptied during a CT scan when the lid is again open. This relative arrangement of the devices or components of the X-ray source 100, in particular the μP reservoir 210 and the μP collector, in the CT gantry avoids the need for a sophisticated μP conveyor system.

In an embodiment, the X-ray system 400 is selected from the group consisting of a CT imaging system 400, a radiographic imaging system 400, an X-ray system 400 for X-ray diffraction measurements, an X-ray system 400 for X-ray fluorescence measurement a dark-field imaging system, an X-ray irradiation system and an X-ray pulse generator. In a preferred embodiment, the X-ray system 400 is a CT imaging system 100.

According to various embodiments, the X-ray system 400 may utilize the X-ray source 100 in a reflection mode, in a mode where the used X-rays are taken out in longitudinal direction of the particle stream 20 or in a transparent mode.

The X-ray source 100 of the invention has several advantages, at least partly related to the high speed of the μPs in the interaction region 1 and thereby the superior powder density in the interaction region 1. With respect to conventional X-ray targets, the X-ray source 100 of the invention may have reduced size of the origin of X-rays while maintaining the same input power. This will help improving contrast resolution.

Assuming a required target thickness of 5 μm, the net mass of μPs that need to be transferred through the interaction region 1 is expected to be between 0.2 kg (4 s scan with a μP velocity of 60 m/s) and about 20 kg (20 s scan with a μP velocity of 1600 m/s). Hence, the required amount of μPs will be depending on the scan length and the desired velocity of the μPs.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

Behling, R. (2021). Modern Diagnostic X-Ray Sources (2nd ed.). CRC Press. https://doi.org/10.1201/9781003095408

Eschey, C., Lutzmann, S., & Zaeh, M. F. (2009). Examination of the powder spreading effect in Electron Beam Melting (EBM). Proc. of the SFF (Solid Freeform Fabrication) Symposion.

IEC60336. (2020). IEC 60336, 5th ed.—Electrical and loading characteristics of X-ray tube assemblies for medical diagnosis (5th ed.). International Electrotechnical Commission.

Latham, R. (ed. (1995). High voltage vacuum insulation (R. Latham (ed.)). Academic Press.

Mahale, T. R. (2009). Electron Beam Melting of Advanced Materials and Structures [North Carolina State University, Raleigh, NC, USA]. https://repository.lib.ncsu.edu/handle/1840.16/4943

Opydo, W., & Opydo, D. (2016). The role of microparticles in initiating the electric breakdown in high-voltage vacuum insulation systems. Computer Applications in Electrical Engineering, 14, 177-186. https://doi.org/10.21008/j.1508-4248.2016.0016

Trottenberg, T., Kersten, H., & Neumann, H. (2008). Feasibility of electrostatic microparticle propulsion. New Journal of Physics, 10(6), 063012. https://doi.org/10.1088/1367-2630/10/6/063012

Wang, S., Wang, C., Peng, Z., & Chen, S. (2018). A new technique for nanoparticle transport and its application in a novel nano-sieve. Scientific Reports, 8(1), 9682. https://doi.org/10.1038/s41598-018-28033-5

The invention claimed is:

1. An X-ray source comprising:
 a microparticle source configured to generate a particle stream of spatially separated and moving, solid and/or liquid microparticles; and
 an electron source configured to generate an electron beam of electrons incident onto the particle stream at an interaction region to excite solid and/or liquid microparticles in the interaction region to generate X-rays.

2. The X-ray source according to claim 1, wherein the microparticle source comprises:
 a microparticle reservoir comprising solid microparticles and/or a liquid; and
 a particle pre-accelerator configured to accelerate the solid microparticles and/or liquid microparticles produced from the liquid.

3. The X-ray source according to claim 2, wherein the particle pre-accelerator comprises a particle guide connected to the microparticle reservoir and arranged relative to the microparticle reservoir to enable a gravitational or centrifugal force acting on the solid microparticles and/or liquid in the microparticle reservoir to transfer solid and/or liquid microparticles from the microparticle reservoir and through the particle guide.

4. The X-ray source according to claim 2, wherein the particle pre-accelerator comprises at least one rotating member having at least one envelope surface configured to engage incident solid and/or liquid microparticles and transfer kinetic energy to the solid and/or liquid microparticles.

5. The X-ray source according to claim 1, wherein the microparticle source comprises:
   a microparticle reservoir comprising solid microparticles and/or a liquid; and
   a particle charger configured to charge solid microparticles transferred from the microparticle reservoir and/or liquid microparticles produced from the liquid in the microparticle reservoir into solid and/or liquid, charged microparticles.

6. The X-ray source according to claim 5, wherein the particle charger comprises:
   a first electrode plate; and
   a second electrode plate arranged in vicinity of the first electrode plate and comprising an aperture, wherein solid and/or liquid microparticles engaging the first electrode plate become electrically charged to obtain solid and/or liquid, electrically charged microparticles drawn by an electric field between the first electrode plate and the second electrode plate towards the second electrode plate and through the aperture.

7. The X-ray source according to claim 5, wherein the particle charger comprises a particle heater configured to heat the solid and/or liquid microparticles.

8. The X-ray source according to claim 5, wherein the particle charger comprises:
   a plurality of bores in a dielectric material; and
   at least two electrodes configured to apply an electric field to polarize the dielectric material, wherein the plurality of bores comprises solid microparticles.

9. The X-ray source according to claim 1, wherein the microparticle source comprises:
   a microparticle reservoir comprising solid microparticles and/or a liquid; and
   a particle magnetizer configured to magnetize solid microparticles transferred from the microparticle reservoir and/or liquid microparticles produced from the liquid in the microparticle reservoir into solid and/or liquid, magnetic microparticles.

10. The X-ray source according to claim 1, wherein the microparticle source comprises a particle accelerator configured to accelerate the solid and/or liquid microparticles to an average velocity of solid and/or liquid microparticles in the interaction region equal to or exceeding a minimum average velocity.

11. The X-ray source according to claim 10, wherein the particle accelerator comprises a mechanical particle accelerator configured to apply a mechanical force onto the solid and/or liquid microparticles to accelerate the solid and/or liquid microparticles.

12. The X-ray source according to claim 10, wherein
   the solid and/or liquid microparticles are solid and/or liquid, magnetic microparticles; and
   the particle accelerator comprises a magnetic particle accelerator configured to generate a gradient magnetic field to accelerate the solid and/or liquid, magnetic microparticles.

13. The X-ray source according to claim 10, wherein
   the solid and/or liquid microparticles are solid and/or liquid, electrically charged microparticles; and
   the particle accelerator comprises an electric particle accelerator configured to generate an electric field to accelerate the solid and/or liquid, electrically charged microparticles.

14. The X-ray source according to claim 1, wherein
   the solid and/or liquid microparticles are solid and/or liquid, electrically charged microparticles; and
   the microparticle source comprises at least two electrodes at different potentials to generate a respective focusing electric field between two adjacent electrodes of the at least two electrodes, the respective focusing electric field is configured to, at least partially, balance repulsive forces in the particle stream at the interaction region.

15. The X-ray source according to claim 1, wherein the microparticle source comprises a nozzle arranged upstream of the interaction region and configured to focus the particle stream at the interaction region.

16. The X-ray source according to claim 1, further comprising an off-focal blocking element comprising an aperture arranged in vicinity of the interaction region, wherein the off-focal blocking element is arranged to block off-focal X-rays generated at the interaction region while passing focal X-rays through the aperture.

17. The X-ray source according to claim 1, further comprising a magnetic source configured to provide a magnetic field directed substantially perpendicular to the particle stream and arranged to deflect electrons scattered in the interaction region in a direction substantially parallel to the particle stream.

18. The X-ray source according to claim 1, further comprising a particle post-accelerator configured to provide an electric field downstream of the interaction region to reduce a density of the solid and/or liquid microparticles in the particle stream downstream of the interaction region.

19. The X-ray source according to claim 1, further comprising a particle decelerator arranged downstream of the interaction region and configured decelerate and reduce a velocity of the solid and/or liquid microparticles.

20. The X-ray source according to claim 19, wherein
   the solid and/or liquid microparticles are solid and/or liquid, electrically charged microparticles; and
   the particle decelerator comprises an electrostatic decelerator comprising at least two electrodes arranged to provide a decelerating electric field configured to decelerate and reduce a velocity of the solid and/or liquid, electrically charged microparticles.

21. The X-ray source according to claim 19, wherein the particle decelerator comprises a mechanical decelerator arranged to mechanically interact with the solid and/or liquid microparticles to reduce a kinetic energy of the solid and/or liquid microparticles.

22. The X-ray source according to claim 19, wherein
   the solid and/or liquid microparticles are solid and/or liquid, magnetic microparticles; and
   the particle decelerator comprises a magnetic particle decelerator arranged to provide a gradient magnetic field configured to reduce a kinetic energy of the solid and/or liquid, magnetic microparticles.

23. The X-ray source according to claim 1, wherein the solid and/or liquid microparticles are solid and/or liquid, electrically charged microparticles, and the X-ray source further comprises a particle de-charger arranged upstream and/or downstream of the interaction region and configured to de-charge solid and/or liquid, electrically charged microparticles.

24. The X-ray source according to claim 1, further comprising a microparticle collector arranged downstream of the interaction region and configured to collect solid microparticles and/or liquid volume formed by the liquid microparticles.

25. The X-ray source according to claim 24, wherein
the microparticle source comprises a microparticle reservoir;
the microparticle collector is connectable to the microparticle reservoir via a particle transport system; and
the microparticle collector is, in use, arranged relative to the microparticle reservoir to transport solid microparticles or liquid from the microparticle collector through the particle transport system and to the microparticle reservoir by gravity.

26. The X-ray source according to claim 1, further comprising:
an electron charge recuperation member comprising at least one electrode arranged downstream of the interaction region and configured to collect a charge from electrons downstream of the interaction region; and
a power supply connected to the microparticle source and/or the electron source and configured to supply power to the microparticle source and/or the electron source, wherein the electron charge recuperation member is connected to the power supply and configured to supply, to the power supply, power generated based on the collected charge.

27. The X-ray source according to claim 1, wherein the solid and/or liquid microparticles are solid and/or liquid, electrically charged microparticles, and the X-ray source further comprises:
a particle charge recuperation member comprising at least one electrode arranged downstream of the interaction region and configured to collect a charge from solid or liquid, electrically charged microparticles downstream of the interaction region; and
a power supply connected to the microparticle source and/or the electron source and configured to supply power to the microparticle source and/or the electron source, wherein the particle charge recuperation member is connected to the power supply and configured to supply, to the power supply, power generated based on the collected charge.

28. The X-ray source according to claim 1, wherein the microparticle source is configured to generate a particle stream of spatially separated and moving, solid and/or liquid microparticles having an average diameter selected within a range of from 0.5 µm up to 1 µm.

29. The X-ray source according to claim 28, wherein the microparticle source is configured to generate a particle stream having, at the interaction region, an average diameter selected within a range of from 1 µm up to 1000 µm.

30. The X-ray source according to claim 1, wherein the microparticle source is configured to generate a particle stream of spatially separated and moving, solid tungsten microparticles.

31. The X-ray source according to claim 1, wherein the microparticle source is configured to generate a particle stream of spatially separated and moving, solid and/or liquid microparticles having an average velocity at the interaction region of at least 500 m/s.

32. The X-ray source according to claim 1, further comprising a vacuum chamber, wherein
the microparticle source is configured to generate the particle stream inside the vacuum chamber; and
the electron source is configured to generate the electron beam incident onto the particle stream at the interaction region inside the vacuum chamber.

33. The X-ray source according to claim 1, wherein
the microparticle source is configured to generate multiple particle streams of spatially separated and moving, solid and/or liquid microparticles in the interaction region; and
the electron source is configured to generate the electron beam of electrons incident onto the multiple particle streams at the interaction region to excite solid and/or liquid microparticles in the interaction region to generate X-rays.

34. The X-ray source according to claim 1, further comprising an electron transparent window separating the electron source from the interaction region, wherein the electron transparent window is transparent for electrons but substantially intransparent for residual gas, vapor and/or the solid and/or liquid microparticles.

35. The X-ray source according to claim 34, wherein the microparticle source is configured to generate the particle stream of spatially separated and moving, solid and/or liquid microparticles embedded in a jet of a gas.

36. An X-ray system comprising an X-ray source according to claim 1.

37. The X-ray system according to claim 36, wherein the X-ray system is selected from the group consisting of a computed tomography (CT) imaging system, a radiographic imaging system, an X-ray system for X-ray diffraction measurements, and an X-ray system for X-ray fluorescence measurement.

* * * * *